(12) United States Patent
Libanati et al.

(10) Patent No.: US 10,835,495 B2
(45) Date of Patent: Nov. 17, 2020

(54) COMPOSITIONS CONTAINING A BIOLOGICALLY ACTIVE MATERIAL AND A NON-ORDERED INORGANIC OXIDE MATERIAL AND METHODS OF MAKING AND USING THE SAME

(71) Applicants: W. R. Grace & Co.-Conn., Columbia, MD (US); Formac Pharmaceuticals N.V., Leuven (BE)

(72) Inventors: Cristian Libanati, Silver Spring, MD (US); Michiel Van Speybroeck, Leuven (BE); Frederik Hendrik Monsuur, Hasselt (BE)

(73) Assignees: W. R. Grace & Co.-Conn., Columbia, MD (US); Formac Pharmaceuticals N.V., Leuven (BE)

( * ) Notice: Subject to any disclaimer, the term of this patent is extended or adjusted under 35 U.S.C. 154(b) by 340 days.

(21) Appl. No.: 14/442,195

(22) PCT Filed: Nov. 13, 2013

(86) PCT No.: PCT/US2013/069921
§ 371 (c)(1),
(2) Date: May 12, 2015

(87) PCT Pub. No.: WO2014/078435
PCT Pub. Date: May 22, 2014

(65) Prior Publication Data
US 2016/0303048 A1 Oct. 20, 2016

Related U.S. Application Data

(60) Provisional application No. 61/726,193, filed on Nov. 14, 2012.

(51) Int. Cl.
| | | |
|---|---|---|
| A61K 9/14 | (2006.01) | |
| A61K 31/216 | (2006.01) | |
| A61K 31/397 | (2006.01) | |
| A61K 31/4985 | (2006.01) | |
| A61K 31/496 | (2006.01) | |
| A61K 31/58 | (2006.01) | |

(52) U.S. Cl.
CPC ............ *A61K 9/143* (2013.01); *A61K 31/216* (2013.01); *A61K 31/397* (2013.01); *A61K 31/496* (2013.01); *A61K 31/4985* (2013.01); *A61K 31/58* (2013.01)

(58) Field of Classification Search
None
See application file for complete search history.

(56) References Cited

U.S. PATENT DOCUMENTS

| | | | |
|---|---|---|---|
| 4,157,920 A | 6/1979 | Wason et al. .................. 106/292 |
| 5,256,386 A | 10/1993 | Nystrom et al. ............... 423/338 |
| 5,506,248 A | 4/1996 | Nikfar et al. ................... 514/374 |
| 5,591,453 A | 1/1997 | Ducheyne et al. ........... 424/484 |
| 5,622,684 A | 4/1997 | Pinnavala et al. ............ 423/702 |
| 5,785,977 A | 7/1998 | Breithbarth ..................... 424/401 |
| 5,817,327 A | 10/1998 | Ducheyne et al. ........... 424/425 |
| 5,830,509 A | 11/1998 | West et al. ..................... 424/489 |
| 5,849,331 A | 12/1998 | Ducheyne et al. ........... 424/484 |
| 5,861,176 A | 1/1999 | Ducheyne et al. ........... 424/486 |
| 5,871,777 A | 2/1999 | Ducheyne et al. ........... 424/486 |
| 5,874,109 A | 2/1999 | Ducheyne et al. ........... 424/486 |
| 5,891,469 A | 4/1999 | Amselem ....................... 424/451 |
| 5,897,876 A | 4/1999 | Rudnic et al. ................. 424/455 |
| 5,951,962 A | 9/1999 | Muller et al. .................. 423/702 |
| 5,989,583 A | 11/1999 | Amselem ....................... 424/439 |
| 6,027,746 A | 2/2000 | Lech ............................. 424/455 |
| 6,048,546 A | 4/2000 | Sasaki et al. .................. 424/450 |
| 6,110,498 A | 8/2000 | Rudnic et al. ................. 424/473 |
| 6,184,220 B1 | 2/2001 | Turck et al. ................ 514/226.5 |
| 6,221,326 B1 | 4/2001 | Amiche ......................... 423/335 |
| 6,248,363 B1 | 6/2001 | Patel et al. ..................... 424/497 |
| 6,414,043 B1 | 7/2002 | Asher et al. ..................... 521/61 |
| 6,511,668 B1 | 1/2003 | Shio et al. ...................... 424/401 |
| 6,551,617 B1 | 4/2003 | Corbo et al. ................... 424/465 |
| 6,592,764 B1 | 7/2003 | Stucky et al. ................. 210/660 |
| 6,617,356 B2 | 9/2003 | Goodman et al. ............. 514/565 |
| 6,699,506 B1 | 3/2004 | Paillard et al. ................ 424/489 |
| 6,726,933 B2 | 4/2004 | Shio et al. ...................... 424/489 |
| 6,764,690 B2 | 7/2004 | Ahola et al. ................... 424/422 |

(Continued)

FOREIGN PATENT DOCUMENTS

| | | | |
|---|---|---|---|
| EP | 0371431 | 6/1990 | ............. A61K 9/18 |
| EP | 0241126 | 7/1991 | ............. A61K 31/19 |

(Continued)

OTHER PUBLICATIONS

Jia et al., "A novel nanomatrix system consisted of colloidal silica and pH-sensitive polymethacrylate improves the oral bioavailability of fenofibrate", May 2011, European Journal of Pharmaceutics and Biopharmaceutics, vol. 79, pp. 126-134.*

Kinnari et al., "Comparison of mesoporous silicon and non-ordered mesoporous silica materials as drug carriers for itraconazole", May 2011, International Journal of Pharmaceutics, vol. 414, pp. 148-156.*

(Continued)

*Primary Examiner* — Hanan S Ahmed
*Assistant Examiner* — Randeep Singh
(74) *Attorney, Agent, or Firm* — Westerman, Hattori, Daniels & Adrian, LLP

(57) ABSTRACT

Compositions containing a biologically active material and a non-ordered inorganic oxide material are disclosed. Methods of making and using compositions containing a biologically active material and a non-ordered inorganic oxide material are also disclosed.

22 Claims, 4 Drawing Sheets

(56) References Cited

U.S. PATENT DOCUMENTS

| | | | |
|---|---|---|---|
| 6,774,179 B2 | 8/2004 | Ferritto et al. | 524/860 |
| 6,905,698 B1 | 6/2005 | Aldcroft et al. | 424/405 |
| 7,112,339 B1 | 9/2006 | Ahola et al. | 424/484 |
| 7,160,555 B2 | 1/2007 | Ouchi et al. | 424/468 |
| 7,160,556 B2 | 1/2007 | Ouichi et al. | 424/468 |
| 7,166,301 B1 | 1/2007 | Ouchi et al. | 424/468 |
| 7,189,417 B2 | 3/2007 | Chen et al. | 424/501 |
| 7,258,874 B2 | 8/2007 | Barbe et al. | 424/501 |
| 7,326,422 B2 | 2/2008 | Ahola et al. | 424/426 |
| 7,354,602 B2 | 4/2008 | Barbe et al. | 424/501 |
| 7,354,603 B2 | 4/2008 | Barbe et al. | 424/501 |
| 7,357,948 B2 | 4/2008 | Jean et al. | 424/501 |
| 7,374,774 B2 | 5/2008 | Bowlin et al. | 424/423 |
| 7,485,318 B2 | 2/2009 | Koskinen et al. | 424/426 |
| 7,498,309 B2 | 3/2009 | Levy | 514/15 |
| 7,575,762 B2 | 8/2009 | Shinoda et al. | 424/490 |
| 7,585,521 B2 | 9/2009 | Barbe | 424/501 |
| 7,727,543 B2 | 6/2010 | Koskinen et al. | 424/426 |
| 7,749,521 B2 | 7/2010 | Martens et al. | 424/400 |
| 7,829,120 B2 | 11/2010 | Gervais et al. | 424/489 |
| 7,829,595 B2 | 11/2010 | Lawrence | 514/579 |
| 7,851,502 B2 | 12/2010 | Bindra et al. | 514/460 |
| 7,897,166 B1 | 3/2011 | Jokinen et al. | 424/426 |
| 7,935,416 B2 | 5/2011 | Yang et al. | 428/312.8 |
| 7,947,312 B2 | 5/2011 | Pero | 424/725 |
| 8,007,824 B2 | 8/2011 | Rigassi-Dietrich | 424/464 |
| 8,101,207 B2 | 1/2012 | Miura et al. | 424/489 |
| 8,105,630 B2 | 1/2012 | Miura et al. | 424/489 |
| 8,124,124 B2 | 2/2012 | Sherry et al. | 424/464 |
| 8,133,301 B2 | 3/2012 | Hwang et al. | 95/27 |
| 8,226,985 B2 | 7/2012 | Fukushima et al. | 424/497 |
| 8,252,337 B2 | 8/2012 | Lee et al. | 424/489 |
| 8,258,137 B2 | 9/2012 | Augustijns et al. | 514/252.1 |
| 8,273,371 B2 | 9/2012 | Martens et al. | 424/452 |
| 8,372,449 B2 | 2/2013 | Pero | 424/725 |
| 8,389,018 B2 | 3/2013 | Jaim et al. | 424/602 |
| 8,440,229 B2 | 5/2013 | Trogler et al. | 424/489 |
| 8,465,769 B2 | 6/2013 | Petereit et al. | 424/463 |
| 8,722,094 B2 | 5/2014 | Yoshida et al. | 424/489 |
| 2002/0032246 A1 | 3/2002 | Asher | 521/64 |
| 2003/0003149 A1 | 1/2003 | Sharma et al. | 424/470 |
| 2003/0021820 A1 | 1/2003 | Ahola et al. | 424/422 |
| 2003/0158263 A1 | 8/2003 | Radhakrishnan et al. | 514/649 |
| 2003/0175343 A1 | 9/2003 | Razus et al. | 424/468 |
| 2003/0203026 A1 | 10/2003 | Sherry et al. | 424/469 |
| 2003/0206859 A1 | 11/2003 | Chen et al. | 424/9.1 |
| 2004/0120971 A1 | 6/2004 | Koskinen et al. | 424/204.1 |
| 2004/0142041 A1 | 7/2004 | MacDonald et al. | 424/489 |
| 2004/0170694 A1 | 9/2004 | Colic | 424/490 |
| 2004/0191320 A1 | 9/2004 | Canham et al. | 424/489 |
| 2004/0197414 A1 | 10/2004 | Ahola et al. | 424/489 |
| 2005/0014681 A1 | 1/2005 | Minamitake et al. | 514/6 |
| 2005/0238675 A1 | 10/2005 | Li et al. | 424/400 |
| 2006/0171969 A1 | 8/2006 | Macelloni et al. | 424/400 |
| 2006/0286165 A1 | 12/2006 | Ge et al. | 424/464 |
| 2006/0293327 A1 | 12/2006 | Hiroshi et al. | 514/247 |
| 2007/0003492 A1 | 1/2007 | Kitahata et al. | 424/49 |
| 2007/0071806 A1 | 3/2007 | McCarty | 424/451 |
| 2007/0128273 A1 | 6/2007 | Miura et al. | 424/464 |
| 2007/0254038 A1 | 11/2007 | Ducheyne et al. | 424/490 |
| 2007/0275068 A1 | 11/2007 | Martens et al. | 424/484 |
| 2007/0286903 A1 | 12/2007 | Becicka et al. | 424/472 |
| 2008/0063711 A1 | 3/2008 | Grenier et al. | 424/472 |
| 2008/0081069 A1 | 4/2008 | Prasad et al. | 424/468 |
| 2008/0081070 A1 | 4/2008 | Wilson et al. | 424/482 |
| 2008/0214677 A1 | 9/2008 | Badwan et al. | 514/646 |
| 2008/0220026 A1 | 9/2008 | Maitra et al. | |
| 2008/0233187 A1 | 9/2008 | Svoboda et al. | 424/456 |
| 2008/0241123 A1 | 10/2008 | Chowdhury | 424/125 |
| 2008/0249076 A1 | 10/2008 | Holm et al. | 514/176 |
| 2008/0260839 A1 | 10/2008 | Canham et al. | 424/489 |
| 2008/0286371 A1 | 11/2008 | Pacheco et al. | 424/491 |
| 2009/0028940 A1 | 1/2009 | Jahagirdar et al. | 424/468 |
| 2009/0041838 A1 | 2/2009 | Guimberteau et al. | 424/452 |
| 2009/0104245 A1 | 4/2009 | Koskinen et al. | 424/423 |
| 2009/0192205 A1 | 7/2009 | Augustijns et al. | 514/384 |
| 2009/0232899 A1 | 9/2009 | David et al. | 424/501 |
| 2009/0324695 A1 | 12/2009 | Ducheyne et al. | 424/445 |
| 2010/0008990 A1 | 1/2010 | Martens et al. | 424/484 |
| 2010/0009001 A1 | 1/2010 | Armes et al. | 424/490 |
| 2010/0015027 A1 | 1/2010 | Yang | 423/328.1 |
| 2010/0062065 A1 | 3/2010 | Jo et al. | 424/486 |
| 2010/0104650 A1 | 4/2010 | Lee et al. | 424/489 |
| 2010/0278922 A1 | 11/2010 | Vol et al. | 424/489 |
| 2010/0297245 A1 | 11/2010 | Vol et al. | 424/489 |
| 2010/0330366 A1 | 12/2010 | Keiser et al. | 428/402 |
| 2010/0331431 A1 | 12/2010 | Keiser et al. | 516/79 |
| 2011/0020455 A1 | 1/2011 | Yoshida et al. | |
| 2011/0086099 A9 | 4/2011 | Martens et al. | 424/484 |
| 2011/0123601 A1 | 5/2011 | Ho et al. | 424/450 |
| 2011/0171097 A1 | 7/2011 | Chung et al. | 423/325 |
| 2011/0256184 A1* | 10/2011 | Lei | A61K 47/02 424/400 |

FOREIGN PATENT DOCUMENTS

| | | | |
|---|---|---|---|
| EP | 0298062 | 9/1991 | C01B 33/16 |
| EP | 0315414 | 10/1991 | A61K 9/54 |
| EP | 0196700 | 1/1992 | A61K 9/16 |
| EP | 0336014 | 6/1992 | A61K 9/18 |
| EP | 0587065 | 1/1997 | A61K 9/20 |
| EP | 0524579 | 3/1998 | A61K 31/70 |
| EP | 0657161 | 12/1998 | A61K 9/16 |
| EP | 0966966 | 12/1999 | A61K 31/495 |
| EP | 0659406 | 3/2000 | A61K 9/20 |
| EP | 0758889 | 8/2000 | A61K 31/19 |
| EP | 0897414 | 9/2001 | C09C 1/30 |
| EP | 0831059 | 12/2001 | C01B 33/12 |
| EP | 1041972 | 9/2002 | A61K 9/20 |
| EP | 0735863 | 11/2002 | A61K 9/20 |
| EP | 0830314 | 12/2002 | C01B 39/00 |
| EP | 0772436 | 3/2003 | A61K 9/16 |
| EP | 1108431 | 5/2003 | A61K 31/54 |
| EP | 0747050 | 9/2003 | A61K 31/415 |
| EP | 1140034 | 11/2003 | A61K 9/22 |
| EP | 1080721 | 1/2004 | A61K 31/00 |
| EP | 0922386 | 2/2004 | A01N 25/10 |
| EP | 1206268 | 10/2004 | A61K 31/727 |
| EP | 1466610 | 10/2004 | A61K 38/00 |
| EP | 1488811 | 12/2004 | A61K 47/10 |
| EP | 0906243 | 8/2005 | C01B 33/16 |
| EP | 1618895 | 1/2006 | A61K 47/02 |
| EP | 1618896 | 1/2006 | A61K 47/02 |
| EP | 1414409 | 2/2007 | A61K 9/10 |
| EP | 1757269 | 2/2007 | A61K 9/12 |
| EP | 1144323 | 7/2007 | C03C 13/06 |
| EP | 1839658 | 10/2007 | A61K 31/353 |
| EP | 1759711 | 6/2008 | A61K 47/02 |
| EP | 1985287 | 10/2008 | A61K 9/16 |
| EP | 1638888 | 5/2009 | C01B 37/02 |
| EP | 2067471 | 6/2009 | A61K 9/48 |
| EP | 2135601 | 12/2009 | A61K 9/16 |
| EP | 1104290 | 3/2010 | A61K 9/28 |
| EP | 1683516 | 6/2010 | A61K 9/14 |
| EP | 1257259 | 7/2010 | A61K 9/22 |
| EP | 1789170 | 7/2010 | B01F 17/00 |
| EP | 2218444 | 8/2010 | A61K 9/20 |
| EP | 1372727 | 9/2010 | A61K 47/04 |
| EP | 2223702 | 9/2010 | A61K 47/04 |
| EP | 2251038 | 11/2010 | A61K 47/04 |
| EP | 1275391 | 3/2011 | A61K 31/415 |
| EP | 1686962 | 5/2011 | A61K 9/14 |
| EP | 1738751 | 5/2011 | A61K 9/50 |
| EP | 2316418 | 5/2011 | A61K 9/00 |
| EP | 2322179 | 5/2011 | A61K 31/485 |
| EP | 3219495 | 5/2011 | A61K 9/14 |
| EP | 2335688 | 6/2011 | A61K 9/16 |
| EP | 2336086 | 6/2011 | C01B 37/02 |
| EP | 0872447 | 7/2011 | C01B 33/18 |
| EP | 1337240 | 7/2011 | A61K 9/14 |
| EP | 1558645 | 7/2011 | C07K 16/18 |
| EP | 1794764 | 7/2011 | H01F 1/00 |
| EP | 2343045 | 7/2011 | A61K 9/00 |
| EP | 2359694 | 8/2011 | A01N 59/00 |

(56) References Cited

FOREIGN PATENT DOCUMENTS

| | | | |
|---|---|---|---|
| EP | 2361616 | 8/2011 | A61K 9/28 |
| EP | 2366387 | 9/2011 | A61K 9/51 |
| EP | 2374479 | 10/2011 | A61K 47/48 |
| EP | 2386308 | 11/2011 | A61K 33/44 |
| EP | 2229938 | 12/2011 | A61K 9/20 |
| EP | 2520583 | 11/2012 | C07K 1/14 |
| EP | 2522674 | 11/2012 | C07K 1/14 |
| EP | 2570121 | 3/2013 | A61K 9/24 |
| EP | 1599186 | 4/2013 | A61K 9/00 |
| EP | 1852393 | 4/2013 | C01B 37/02 |
| EP | 2620152 | 7/2013 | A61K 31/545 |
| EP | 2364694 | 11/2013 | A61K 9/20 |
| EP | 2669269 | 12/2013 | C07C 239/00 |
| EP | 2366379 | 4/2015 | A61K 9/16 |
| GB | 1572718 | 7/1980 | A01N 17/08 |
| JP | 10-045974 A | 2/1998 | |
| JP | 10175994 | 6/1998 | C07H 21/04 |
| JP | 11246404 | 9/1999 | A61K 47/02 |
| JP | 2005-221655 A | 8/2005 | |
| JP | 2006248832 | 9/2006 | C01B 33/12 |
| JP | 2010-211027 A | 9/2010 | |
| WO | 9528404 | 10/1995 | C07D 491/22 |
| WO | 9603117 | 2/1996 | A61K 9/16 |
| WO | 9741839 | 11/1997 | A61K 9/50 |
| WO | 9745367 | 12/1997 | C01B 33/16 |
| WO | 9824436 | 6/1998 | A61K 31/47 |
| WO | 9903471 | 1/1999 | A61K 31/445 |
| WO | 9909957 | 3/1999 | A61K 9/20 |
| WO | 9917766 | 4/1999 | A61K 31/21 |
| WO | 9937705 | 7/1999 | C08J 9/00 |
| WO | 0009093 | 2/2000 | A61K 9/28 |
| WO | 0037055 | 6/2000 | A61K 9/22 |
| WO | 0050349 | 8/2000 | C03B 37/00 |
| WO | 0112221 | 2/2001 | A61K 39/385 |
| WO | 0113924 | 3/2001 | A61K 31/727 |
| WO | 0180823 | 11/2001 | A61K 9/00 |
| WO | 02080977 | 10/2002 | A61K 47/04 |
| WO | 2004006904 | 1/2004 | A61K 31/165 |
| WO | 2004032901 | 4/2004 | A61K 9/14 |
| WO | 2004073689 | 9/2004 | A61K 9/18 |
| WO | 2005000740 | 1/2005 | C01B 33/00 |
| WO | 2005020993 | 3/2005 | A61K 31/436 |
| WO | 2005034920 | 4/2005 | A61K 9/20 |
| WO | 2005065662 | 7/2005 | A61K 9/20 |
| WO | 2005087199 | 9/2005 | A61K 9/14 |
| WO | 2005087369 | 9/2005 | B01J 29/00 |
| WO | 2006026840 | 3/2006 | A61K 9/16 |
| WO | 2006031259 | 3/2006 | C01B 39/02 |
| WO | 2006038912 | 4/2006 | C01B 39/02 |
| WO | 2006050533 | 5/2006 | A61K 9/24 |
| WO | 2007001355 | 1/2007 | G01N 33/53 |
| WO | 2007015243 | 2/2007 | B01J 13/02 |
| WO | 2007025715 | 3/2007 | A61K 47/02 |
| WO | 2007042833 | 4/2007 | C01B 31/02 |
| WO | 2007076874 | 7/2007 | A61K 9/20 |
| WO | 2007115381 | 10/2007 | A61K 9/14 |
| WO | 2007127837 | 11/2007 | A61K 38/14 |
| WO | 2008014610 | 2/2008 | A61K 47/12 |
| WO | 2008016260 | 2/2008 | A61K 9/14 |
| WO | 2008028641 | 3/2008 | C08K 9/02 |
| WO | 2008057058 | 5/2008 | A61K 9/20 |
| WO | 2008062429 | 5/2008 | B82B 3/00 |
| WO | 2008077823 | 7/2008 | A61K 9/107 |
| WO | 2008093347 | 8/2008 | A01N 25/26 |
| WO | 2008100032 | 8/2008 | A61K 9/00 |
| WO | 2008101011 | 8/2008 | B82B 3/00 |
| WO | 2008127609 | 10/2008 | A61K 31/40 |
| WO | 2008134013 | 11/2008 | A61K 9/16 |
| WO | 2008137504 | 11/2008 | G01N 33/00 |
| WO | 2008149232 | 12/2008 | A01N 25/08 |
| WO | 2009012791 | 1/2009 | A61K 9/20 |
| WO | 2009013306 | 1/2009 | A61K 9/20 |
| WO | 2009013594 | 1/2009 | A61K 31/55 |
| WO | 2009022355 | 2/2009 | A61K 9/22 |
| WO | 2009023697 | 2/2009 | C01B 33/12 |
| WO | 2009024858 | 2/2009 | A61K 9/20 |
| WO | 2009038659 | 3/2009 | A61K 51/06 |
| WO | 2009044380 | 4/2009 | A61K 9/16 |
| WO | 2009055038 | 4/2009 | A61K 31/70 |
| WO | 2009063257 | 5/2009 | A01N 25/28 |
| WO | 2009064964 | 5/2009 | A61N 1/05 |
| WO | 2009087633 | 7/2009 | A61K 38/21 |
| WO | 2009087634 | 7/2009 | A61K 38/28 |
| WO | 2009088385 | 7/2009 | A61K 9/50 |
| WO | 2009/113522 A1 | 9/2009 | |
| WO | 2009106837 | 9/2009 | C25D 3/02 |
| WO | 2009124982 | 10/2009 | A61K 9/19 |
| WO | 2009128636 | 10/2009 | B82B 3/00 |
| WO | 2009133100 | 11/2009 | C01B 37/02 |
| WO | 2009148990 | 12/2009 | A61K 9/20 |
| WO | 2009150514 | 12/2009 | A61K 9/20 |
| WO | 2009151574 | 12/2009 | A23G 1/22 |
| WO | 2010029571 | 3/2010 | A61K 9/22 |
| WO | 2010053691 | 5/2010 | A61K 31/515 |
| WO | 2010056065 | 5/2010 | A61K 9/58 |
| WO | 2010077774 | 7/2010 | B01J 13/18 |
| WO | 2010082910 | 7/2010 | A61K 9/14 |
| WO | 2010084041 | 7/2010 | A61K 9/20 |
| WO | 2010092925 | 8/2010 | A61K 9/20 |
| WO | 2010096733 | 8/2010 | C09K 11/59 |
| WO | 2010105672 | 9/2010 | A61K 9/50 |
| WO | 2010105673 | 9/2010 | A61K 9/50 |
| WO | 2010128300 | 11/2010 | A61K 9/16 |
| WO | 2010129545 | 11/2010 | A61K 9/22 |
| WO | 2011008484 | 1/2011 | C01B 33/141 |
| WO | 2011008492 | 1/2011 | C01B 33/141 |
| WO | 2011029181 | 3/2011 | A61K 31/216 |
| WO | 2011059981 | 5/2011 | H01M 2/16 |
| WO | 2011068481 | 6/2011 | A61L 24/06 |
| WO | 2011112161 | 9/2011 | A61K 9/20 |
| WO | 2011112723 | 9/2011 | A61M 5/142 |
| WO | 2011117306 | 9/2011 | A61K 9/20 |
| WO | 2011119477 | 9/2011 | A61K 9/48 |
| WO | 201132585 | 10/2011 | C01B 37/02 |
| WO | 2011123110 | 10/2011 | A61L 27/10 |
| WO | 2011128855 | 10/2011 | C09K 11/59 |
| WO | 2011132008 | 10/2011 | A61K 31/554 |
| WO | 2011151087 | 12/2011 | A61K 9/48 |
| WO | 2011154009 | 12/2011 | A61K 31/216 |
| WO | 2011156895 | 12/2011 | H01F 1/00 |
| WO | 2012004291 | 1/2012 | A61K 35/54 |
| WO | 2012007612 | 1/2012 | A61L 27/12 |
| WO | 2012010520 | 1/2012 | A61K 8/64 |
| WO | 2012022919 | 2/2012 | A61K 9/20 |
| WO | 2012076087 | 6/2012 | A61K 9/50 |
| WO | 2012082083 | 6/2012 | A61K 9/14 |
| WO | 2012092283 | 7/2012 | A61K 9/00 |
| WO | 2012131690 | 10/2012 | A61K 8/20 |
| WO | 2012149376 | 11/2012 | A61K 9/16 |
| WO | 2012153181 | 11/2012 | A61K 9/16 |
| WO | 2013012307 | 1/2013 | A61K 9/16 |
| WO | 2013029198 | 3/2013 | A61K 31/675 |
| WO | 2013040295 | 3/2013 | A61K 33/06 |
| WO | 2013048222 | 4/2013 | C07K 14/405 |
| WO | 2013056132 | 4/2013 | A61K 9/16 |
| WO | 2013060304 | 5/2013 | A61K 9/14 |
| WO | 2013110789 | 8/2013 | A61K 9/14 |
| WO | 2013110856 | 8/2013 | A61K 47/02 |
| WO | 2013117122 | 8/2013 | C07K 1/20 |
| WO | 2013170171 | 11/2013 | A61M 37/00 |
| WO | 2013176504 | 11/2013 | G01N 33/53 |
| WO | 2013177147 | 11/2013 | A61K 9/51 |
| WO | 2014006636 | 1/2014 | A61K 9/20 |
| WO | 2015153613 | 10/2015 | A61K 9/14 |

OTHER PUBLICATIONS

Miura et al., "Stability of amorphous drug, 2-benzyl-5-(4-chlorophenyl)-6-[4-(methylthio)phenyl]-2H-pyridazin-3-one, in silica mesopores and measurement of its molecular mobility by solid-state (13)C NMR spectroscopy", International Journal of Pharmaceutics, 2011, vol. 410, pp. 61-67.*

U.S. Appl. No. 61/726,193, filed Nov. 14, 2012.

(56) References Cited

OTHER PUBLICATIONS

Milovic et al.; "Characterization and Evaluation of Solid Self-Microemulsifying Drug Delivery Systems and Porous Carriers as Systems for Improved Carbamazepine Release;" International Journal of Pharmaceutics, 436 (2012), 58-65.

Tang et al.; "Development of Solid Self-Emulsifying Drug Delivery Systems: Preparation Techniques and Dosage Forms;" Drug Discovery Today, vol. 13, No. 13/14 (2008).

Mura et al.; "New Solid Self-Emulsifying Systems to Enhance Dissolution Rate of Poorly Water Soluble Drugs;" Pharmaceutical Development and Technology, (2010), 1-8.

Wang et al. "Solid Self-Emulsifying Nitrendipine Pellets: Preparation and In Vitro / In Vivo Evaluation;" International Journal of Pharmaceutics, 383 (2010), 1-6.

Limnell et al.; "Drug Delivery Formulations of Ordered and Nonordered Mesoporous Silica: Comparison of Three Drug Loading Methods;" Journal of Pharmaceutical Sciences, vol. 100, No. 8 (2011).

Balakrishnan et al.; "Enhanced Oral Bioavailability of Dexibuprofen by a Novel Solid Self-Emulsifying Drug Delivery System (SEDDS);" European Journal of Pharmaceutics and Biopharmaceutics, 72 (2009), 539-545.

Van Speybroeck et al.; "Incomplete Desorption of Liquid Excipients Reduces the In Vitro and in Vivo Performance of Self-Emulsifying Drug Delivery Systems Solidified by Adorption Onto an Inorganic Mesoporous Carrier;" Molecular Pharmaceutics, 4;9(9) (2012), 2750-2760.

Filipovic et al.; "Oil Absorption in Mesoporous Silica Particles;" Processing and Application of Ceramics, 4 (4)(2010), 265-269.

Barbe et al.; "Silica Particles: A Novel Drug-Delivery System;" Advanced Materials, vol. 16, No. 20 (2004).

Hu et al.; "Sirolimus Solid Self-Microemulsifying Pellets: Formulation Development, Characterization and Bioavailability Evaluation;" International Journal of Pharmaceutics, (2012).

Kovacic et al.; "Solid Dispersions of Carvedilol with Porous Silica;" Chemical and Pharmaceutical Bulletin, 59 (4) (2011), 427-433.

PCT Search Report and Written Opinion for PCT/US2013/69921; dated Mar. 7, 2014.

Bamford et al.; "Comprehensive Chemical Kinetics;" Kinetics and Chemical Technology, vol. 23 (1985), 165-166.

Welsh, William; "Ulmann's Encyclopedia of Industrial Chemistry" vol. A.23, Chapter 5. Silica Gel (1993), 629-635.

Fujita, D. et al., "Manufacturing of a Nitrogen Gas Absorbed Amount Measuring Device for Obtaining Fine Pore Information of Mesoporous Silica and Examination of Application of Measured Data in Determination of a Fine Pore Diameter Distribution According to the BJH Theory", Fukushima University, Research Annual Report, No. 6, Jan. 2011, pp. 11-20.

Chaudhari, Smruti P. et al., "Mesoporous Silica as a Carrier for Amorphous Solid Dispersion", British Journal of Pharmaceutical Research, vol. 16, No. 6, 2017, pp. 1-19; Cited in co-pending JP Office Action dated Feb. 21, 2019.

English Translation of Report of Result of Re-examination dated Oct. 3, 2019, issued in counterpart JP application No. 2015-542752. (2 pages).

Office Action dated Jul. 10, 2020, issued in counterpart JP application No. 2019-8301, with English translation. (54 pages).

\* cited by examiner

XRD Diffraction Pattern of Sample Silica 2

XRD Diffraction Pattern of Sample Silica 3

COMPOSITIONS CONTAINING A BIOLOGICALLY ACTIVE MATERIAL AND A NON-ORDERED INORGANIC OXIDE MATERIAL AND METHODS OF MAKING AND USING THE SAME

TECHNICAL FIELD

The present invention relates to compositions containing a biologically active material and a non-ordered inorganic oxide material, methods of making compositions containing a biologically active material and a non-ordered inorganic oxide material, and methods of using compositions containing a biologically active material and a non-ordered inorganic oxide material.

BACKGROUND

Efforts continue in the development of compositions suitable for effective drug bioavailability.

SUMMARY

The present invention continues the effort to develop compositions suitable for effective drug bioavailability by the development of drug release compositions comprising one or more non-ordered inorganic oxide materials and at least one biologically active material incorporated therein. In one exemplary embodiment, the composition of the present invention comprises a biologically active material and an inorganic oxide material, wherein the inorganic oxide material comprises a non-ordered porous material comprising pores having a mean pore diameter of about 2.5 nm to about 15.0 nm, or greater, pores having a pore volume, as measured by nitrogen porosimetry, of about 0.5 cc/g to about 3.0 cc/g, or greater; and a BET surface area, as measured by nitrogen adsorption, of about 300 $m^2$/g up to 1500 $m^2$/g, or greater. In some embodiments, the non-ordered porous material comprising pores having a mean pore diameter of from about 5.0 to about 10.0 nm; pores having a pore volume, as measured by nitrogen porosimetry, of from about 0.7 to about 2.5 cc/g; and a BET surface area, as measured by nitrogen adsorption, of from about 400 to about 1400 $m^2$/g, or greater.

In other embodiments, the inorganic oxide material may have a pore size distribution relative span of at least about 0.4, at least about 0.5, at least about 0.6, at least about 0.7, at least about 0.8, at least about 0.9, at least about 1.0, or at least about 1.1. In further embodiments, the inorganic oxide materials may have a pore size distribution relative span of at least about 0.4, at least about 0.5, at least about 0.6, at least about 0.7, at least about 0.8, at least about 0.9, at least about 1.0, or at least about 1.1, up to about 2.0.

In another exemplary embodiment, the present invention is directed to a composition comprising a biologically active material and an inorganic oxide material, wherein the inorganic oxide material comprises a non-ordered porous material, and wherein as the pore volume increases above about 0.5 cc/g, the surface area ranges from (1) a lower surface area amount represented by a sum of 300 $m^2$/g plus about 27 $m^2$/g per 0.1 cc/g increase in the pore volume above 1.1 cc/g, and (2) an upper surface area amount represented by a sum of 800 $m^2$/g plus about 160 $m^2$/g per 0.1 cc/g increase in the pore volume above 0.5 cc/g.

In a further exemplary embodiment, the present invention includes a composition comprising a biologically active material and an inorganic oxide material, wherein the inorganic oxide material comprises two or more different and distinct types of non-ordered porous material with each distinct type of non-ordered porous material providing a specific dissolution rate profile for the biologically active material so as to form a composite dissolution rate profile for the biologically active material.

In another exemplary embodiment, the present invention is directed to a pharmaceutical composition comprising at least one pharmaceutical dosage formulating ingredient; and a drug release composition comprising a biologically active material and an inorganic oxide material, wherein the inorganic oxide material comprises a non-ordered porous material comprising pores having a mean pore diameter of about 2.5 nm to about 15.0 nm, or greater, pores having a pore volume, as measured by nitrogen porosimetry, of about 0.5 cc/g to about 3.0 cc/g, or greater; and a BET surface area, as measured by nitrogen adsorption, of about 300 $m^2$/g to about 1400 $m^2$/g, or greater. In other embodiments, the inorganic oxide material may have a pore size distribution relative span of at least about 0.4, at least about 0.5, at least about 0.6, at least about 0.7, at least about 0.8, at least about 0.9, at least about 1.0, or at least about 1.1. In further embodiments, the inorganic oxide materials may have a pore size distribution relative span of at least about 0.4, at least about 0.5, at least about 0.6, at least about 0.7, at least about 0.8, at least about 0.9, at least about 1.0, or at least about 1.1, up to about 2.0.

In another exemplary embodiment, the present invention is directed to a pharmaceutical composition comprising at least one pharmaceutical dosage formulating ingredient; and a drug release composition comprising a biologically active material and an inorganic oxide material, wherein the inorganic oxide material comprises a non-ordered porous material, and wherein as the pore volume increases above about 0.5 cc/g, the surface area ranges from (1) a lower surface area amount represented by a sum of 300 $m^2$/g plus about 27 $m^2$/g per 0.1 cc/g increase in the pore volume above 1.1 cc/g, and (2) an upper surface area amount represented by a sum of 800 $m^2$/g plus about 160 $m^2$/g per 0.1 cc/g increase in the pore volume above 0.5 cc/g.

In a further exemplary embodiment, the present invention includes a pharmaceutical composition comprising at least one pharmaceutical dosage formulating ingredient; and a drug release composition comprising a biologically active material and an inorganic oxide material, wherein the inorganic oxide material comprises two or more different and distinct types of non-ordered porous material with each distinct type of non-ordered porous material providing a specific dissolution rate profile for the biologically active material so as to form a composite dissolution rate profile for the biologically active material.

The present invention is further directed to methods of making the disclosed compositions. In one exemplary embodiment, the method of making a composition of the present invention comprises incorporating at least one biologically active material into inorganic oxide material, wherein the inorganic oxide material comprises a non-ordered porous material comprising pores having a mean pore diameter of about 25 angstroms to about 150 angstroms; pores having a pore volume, as measured by nitrogen porosimetry, of about 0.5 cc/g or greater; and a BET surface area, as measured by nitrogen adsorption, of about 300 $m^2$/g or greater. In some embodiments, the method comprises combining a drug release composition comprising the at least one biologically active material and the inorganic oxide material with at least one pharmaceutical dosage formulating ingredient so as to form a pharmaceutical composition.

In another exemplary embodiment, the present invention is directed to a method of making a composition by incorporating at least one biologically active material into inorganic oxide material, wherein the inorganic oxide material comprises a non-ordered porous material, and wherein as the pore volume increases above about 0.5 cc/g, the surface area ranges from (I) a lower surface area amount represented by a sum of 300 $m^2/g$ plus about 27 $m^2/g$ per 0.1 cc/g increase in the pore volume above 1.1 cc/g, and (2) an upper surface area amount represented by a sum of 800 $m^2/g$ plus about 160 $m^2/g$ per 0.1 cc/g increase in the pore volume above 0.5 cc/g.

In a further exemplary embodiment, the present invention includes a method of making a composition by incorporating at least one biologically active material into inorganic oxide material, wherein the inorganic oxide material comprises two or more different and distinct types of non-ordered porous material with each distinct type of non-ordered porous material providing a specific dissolution rate profile for the biologically active material so as to form a composite dissolution rate profile for the biologically active material.

The present invention is even further directed to methods of using the disclosed compositions. In one exemplary embodiment, the method of using a composition of the present invention comprises administering a composition to a patient so as to deliver a biologically active material to the patient, wherein the composition comprises at least one biologically active material and an inorganic oxide material, wherein the inorganic oxide material comprises a non-ordered porous material comprising pores having a mean pore diameter of about 2.5 nm to about 15.0 nm, or greater; pores having a pore volume, as measured by nitrogen porosimetry, of about 0.5 cc/g to about 3.0 cc/g, or greater; and a BET surface area, as measured by nitrogen adsorption, of about 300 $m^2/g$ to about 1400 $m^2/g$, or greater. In another embodiment, the composition of the present invention possesses an in vitro dissolution rate of a biologically active material of at least about 2 times more than the dissolution rate of the same biologically active material in crystalline form. In a further embodiment, the in vitro dissolution rate of the biologically active material is at least about 2 to about 10, or about 3 to about 10, or about 4 to about 10, or about 5 to about 10 times, more than the dissolution rate of the biologically active material in crystalline form.

In another exemplary embodiment, the present invention is directed to a method of using a composition by administering the composition to a patient so as to deliver a biologically active material to the patient, wherein the composition comprises at least one biologically active material and an inorganic oxide material, wherein the inorganic oxide material comprises a non-ordered porous material, and wherein as the pore volume increases above about 0.5 cc/g, the surface area ranges from (1) a lower surface area amount represented by a sum of 300 $m^2/g$ plus about 27 $m^2/g$ per 0.1 cc/g increase in the pore volume above 1.1 cc/g, and (2) an upper surface area amount represented by a sum of 800 $m^2/g$ plus about 160 $m^2/g$ per 0.1 cc/g increase in the pore volume above 0.5 cc/g.

In a further exemplary embodiment, the present invention includes a method of using a composition by administering the composition to a patient so as to deliver a biologically active material to the patient, wherein the composition comprises at least one biologically active material and an inorganic oxide material, wherein the inorganic oxide material comprises a non-ordered porous material, and wherein the inorganic oxide material comprises two or more different and distinct types of non-ordered porous material with each distinct type of non-ordered porous material providing a specific dissolution rate profile for the biologically active material so as to form a composite dissolution rate profile for the biologically active material.

These and other features and advantages of the present invention will become apparent after a review of the following detailed description of the disclosed embodiments and the appended claims.

BRIEF DESCRIPTION OF THE DRAWINGS

The present invention is further described with reference to the appended figures, wherein.

DETAILED DESCRIPTION

Figure 1:
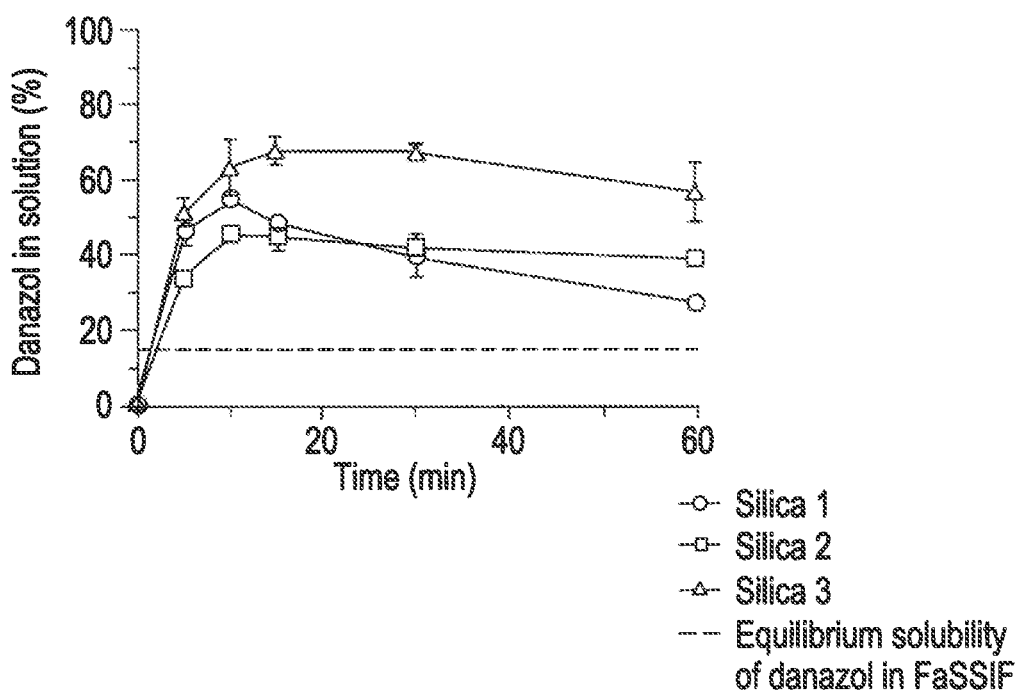
FIG. 1 graphically displays the rate of dissolution over time of an exemplary active pharmaceutical ingredient (API), danazol, from various exemplary non-ordered silicas of the present invention.

To promote an understanding of the principles of the present invention, descriptions of specific embodiments of the invention follow and specific language is used to describe the specific embodiments. It will nevertheless be understood that no limitation of the scope of the invention is intended by the use of specific language. Alterations, further modifications, and such further applications of the principles of the present invention discussed are contemplated as would normally occur to one ordinarily skilled in the art to which the invention pertains.

It must be noted that as used herein and in the appended claims, the singular forms "a", "and", and "the" include plural referents unless the context clearly dictates otherwise. Thus, for example, reference to "an oxide" includes a plurality of such oxides and reference to "oxide" includes reference to one or more oxides and equivalents thereof known to those skilled in the art, and so forth.

"About" modifying, for example, the quantity of an ingredient in a composition, concentrations, volumes, process temperatures, process times, recoveries or yields, flow rates, and like values, and ranges thereof, employed in describing the embodiments of the disclosure, refers to variation in the numerical quantity that may occur, for example, through typical measuring and handling procedures; through inadvertent error in these procedures; through differences in the ingredients used to carry out the methods; and like proximate considerations. The term "about" also encompasses amounts that differ due to aging of a formulation with a particular initial concentration or mixture, and amounts that differ due to mixing or processing a formulation with a particular initial concentration or mixture. Whether modified by the term "about" the claims appended hereto include equivalents to these quantities.

As used herein, the term "biologically active material" means an active pharmaceutical ingredient (API), which provides a pharmacological activity or otherwise have direct effect in the diagnosis, cure, mitigation, treatment or prevention of disease, or to have direct effect in restoring, correcting or modifying physiological functions in humans. Even though this includes poorly soluble material, it may also include materials that range in solubility, including those listed in the BCS (Biopharmaceutic Classification System), which is a classification approach where drugs (APIs) are divided into four classes based on the extent (high or low) of their aqueous solubility and permeability through the GI tract wall, in particular intestinal. In this regard, these four classes are: (Group I) High Solubility and High Permeability drugs, (Group II) Low Solubility and High Permeability drugs, (Group III) High Solubility and Low Permeability drugs and, (Group IV) Low solubility and Low Permeability drugs.

As used herein, "inorganic oxides" is defined as binary oxygen compounds where the inorganic component is the cation and the oxide is the anion. The inorganic material includes metals may also include metalloids. Metals include those elements on the left of the diagonal line drawn from boron to polonium on the periodic table. Metalloids or semi-metals include those elements that are on the right of this line. Examples of inorganic oxides include silica, alumina, titania, zirconia, etc., and mixtures thereof.

As used herein, the term "ordered porous material" refers to porous particles that have structural order with a very narrow pore size distribution and X-ray diffraction patterns such that the pore size distribution has a relative span, as defined herein, of less than 0.3.

Figure 6:
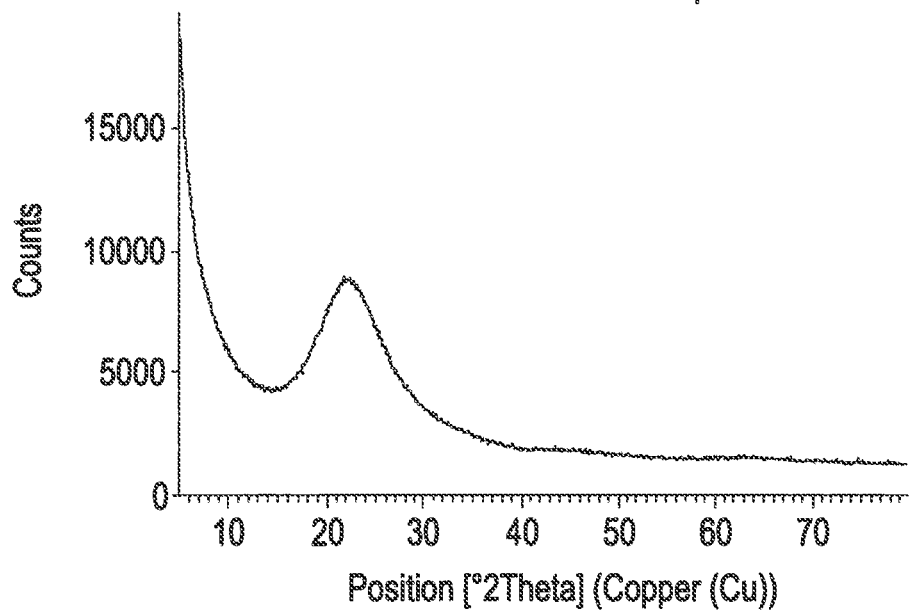
FIGS. 6-8 depict X-ray diffraction patterns of exemplary embodiments of the chromatography media of the present invention.
Figure 7:
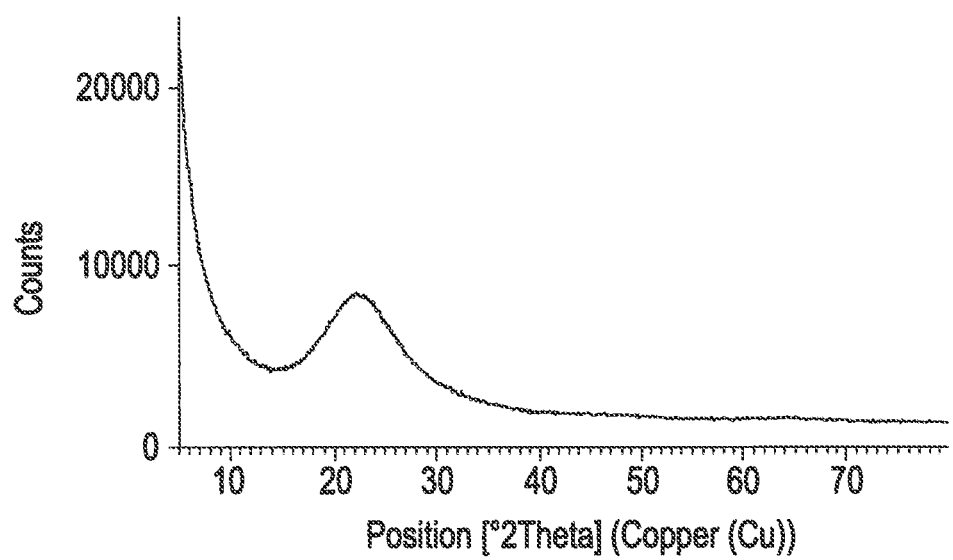
Figure 8:
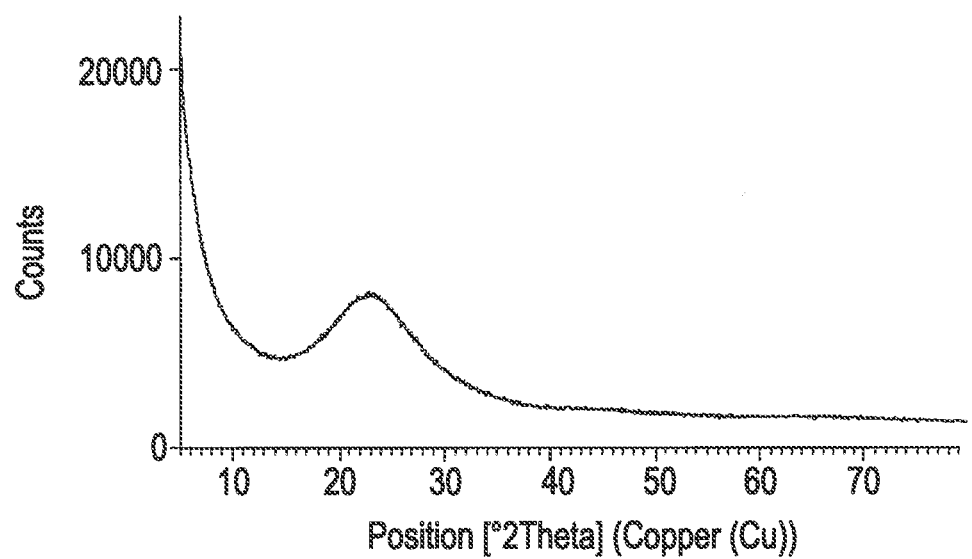

As used herein, the term "non-ordered porous material" refers to porous particles possessing a pore size distribution that is not uniform (i.e., a very broad pore size distribution that is multimodal in nature), such that the pore size distribution has a relative span, as defined herein, of greater than 0.4. In addition, non-ordered porous materials may possess an internal structure such that they do not have a low angle X-ray diffraction pattern, as shown in FIGS. 6-8. Such materials may be formed via any known process including, but not limited to, a solution polymerization process such as for forming colloidal particles, a continuous flame hydrolysis technique such as for forming fused particles, a gel technique such as for forming gelled particles, and a precipitation technique such as for forming precipitated particles. The particles may be subsequently modified by autoclaving, flash drying, super critical fluid extracting, etching, or like processes. The particles may be composed of organic and/or inorganic materials and combinations thereof. In one exemplary embodiment the particles are composed of inorganic materials such as inorganic oxides, sulfides, hydroxides, carbonates, silicates, phosphates, etc, but are preferably inorganic oxides. The particles may be a variety of different symmetrical, asymmetrical or irregular shapes, including chain, rod or lath shape. The particles may have different structures including amorphous or crystalline, etc. The particles may include mixtures of particles comprising different compositions, sizes, shapes or physical structures, or that may be the same except for different surface treatments. Porosity of the particles may be intraparticle or interparticle in cases where smaller particles are agglomerated to form larger particles. In one exemplary embodiment the particles are composed of inorganic materials such as inorganic oxides, sulfides, hydroxides, carbonates, silicates, phosphates, etc, but are preferably inorganic oxides. Porous materials include organic and inorganic materials, or hybrids thereof, and may be in the form of particles, monoliths, membranes, coatings, and the like.

Figure 5:
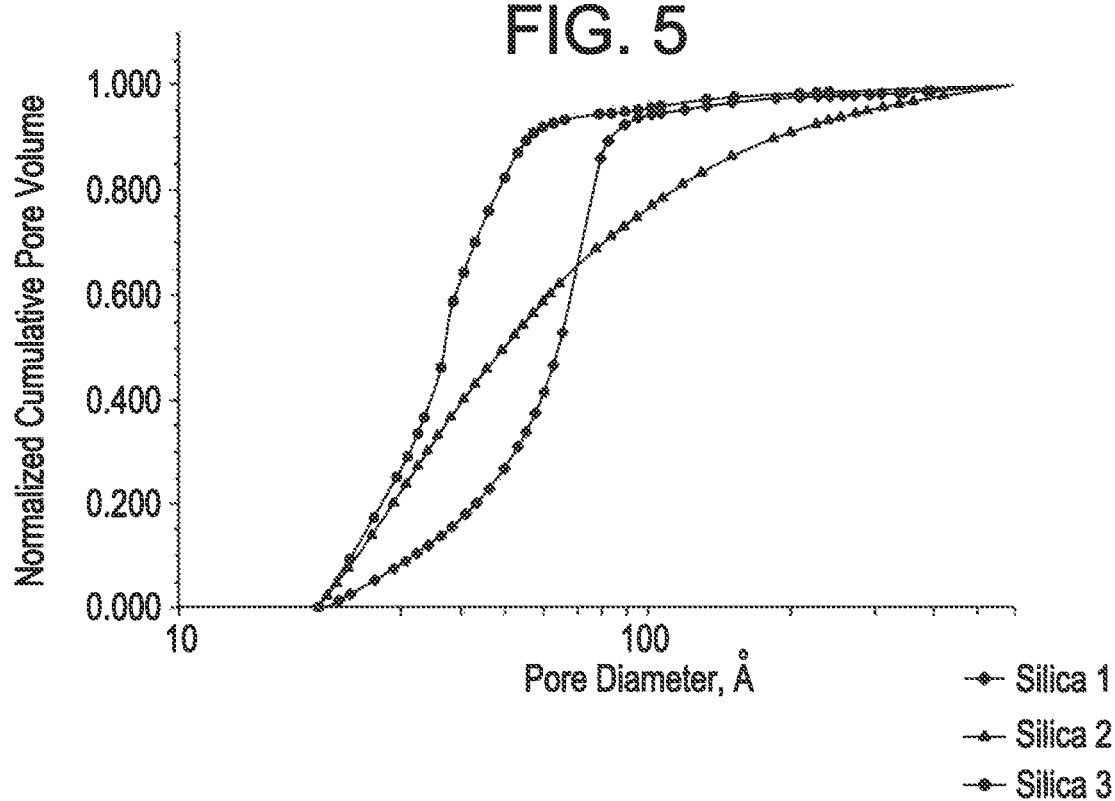
FIG. 5 depicts a graph of pore size distributions of exemplary embodiments of the chromatography media of the present invention.

As used herein, the term "pore size distribution" means the relative abundance of each pore size in a representative volume of porous inorganic particles. As used herein "median pore size" is the pore diameter below which 50% of the intraparticle pore volume resides for pores between 20 and 600 angstroms. See FIG. 5.

As used herein, the term "relative span" is defined as meaning a measure of the breadth of pore size distribution. The "span" is measured by subtracting the $d_{30}$ pore size (i.e., the pore size/diameter below which 30% of the pore volume resides for pores between 20 and 600 angstroms) from the $d_{85}$ pore size (i.e., the pore size/diameter below which 85% by pore volume resides) as measured by mercury porosimetry. The term "relative span" is defined as the ratio of $(d_{85}-d_{30})/d_{50}$.

As used herein, the term "drug bioavailability" means the ability of the human body to absorb biologically active materials, including APIs, which depends upon the solubility of the materials in water.

As used herein, the term "drug release" means the ability of the biologically active material to be released in biological fluids or simulated biological fluids.

As used herein, the term "crystalline" means a solid material whose constituent atoms, molecules, or ions are arranged in an ordered pattern extending in all three directions, which may be measured by X-ray diffraction or differential scanning calorimetry.

As used herein, the term "supersaturation" means a solution that contains more of a dissolved material (i.e., solute) than could be dissolved by a solvent under ambient conditions. This is a measure of the deviation of a dissolved material in a solution from its saturated equilibrium state.

As used herein, the term "dissolution" means the process by which a solid, liquid or a gas forms a solution in a solvent. For dissolution of solids, the process involves the breakdown of the crystal lattice into individual ions, atoms or molecules and their transport into the solvent. Dissolution rates of a biologically active material (e.g., API) are a measure of drug release to determine in vivo bioavailability.

The present invention is directed to compositions comprising a biologically active material and an inorganic oxide material, wherein the inorganic oxide material comprises a non-ordered porous material. Drug bioavailability is a concern for many poorly soluble biologically active materials and this invention relates to various embodiments that provide solutions to this problem. Applicants of the present invention have found that non-ordered porous material having a specific sets of physical properties provide exceptional drug bioavailability properties. In particular, non-ordered porous material comprising (i) pores having a mean pore diameter of about 2.5 nm to about 15.0 nm; (ii) pores having a pore volume, as measured by nitrogen porosimetry, of about 0.5 cc/g to about 3.0 cc/g, or greater, and (iii) a BET surface area, as measured by nitrogen adsorption, of about 300 m$^2$/g to or greater unexpectedly provide exceptional drug bioavailability properties. Further, non-ordered porous material comprising (i) pores having a mean pore diameter of from about 50 to about 100 angstroms; (ii) pores having a pore volume, as measured by nitrogen porosimetry, of from about 0.7 to about 2.5 cc/g; and (iii) a BET surface area, as measured by nitrogen adsorption, of from about 400 to about 1400 m²/g, or greater, unexpectedly provide even more exceptional drug bioavailability properties. In an exemplary embodiment, the non-ordered porous material possesses a loss on ignition of more than about 4%, 5%, 6%, 7%, 8%, 9%, 10%, or more by weight based upon the weight of the non-ordered porous material. In a further exemplary embodiment, the non-ordered porous material possesses a pore volume to In other embodiments, the inorganic oxide material may have a pore size distribution relative span of at least about 0.4, at least about 0.5, at least about 0.6, at least about 0.7, at least about 0.8, at least about 0.9, at least about 1.0, or at least about 1.1. In further embodiments, the inorganic oxide materials may have a pore size distribution relative span of at least about 0.4, at least about 0.5, at least about 0.6, at least about 0.7, at least about 0.8, at least about 0.9, at least about 1.0, or at least about 1.1, up to about 2.0.

In one exemplary embodiment, the present invention is directed to a composition comprising a biologically active material and an inorganic oxide material, wherein the inorganic oxide material comprises a non-ordered porous material comprising (i) pores having a mean pore diameter of about 2.5 nm to about 15.0 nm; (ii) pores having a pore volume, as measured by nitrogen porosimetry, of about 0.5 cc/g to about 2.5 cc/g, or greater; and (iii) a BET surface area, as measured by nitrogen adsorption, of about 300 m²/g to about 1400 m²/g, or greater. In a further embodiment, the non-ordered porous material has a mean pore diameter of from about 3.0 nm to about 14.0 nm, or from about 3.0 nm to about 13.0 nm, or from about 4.0 nm to about 12.0 nm, or from about 4.0 nm to about 11.0 nm, or from about 5.0 nm to about 10.0 nm. In another embodiment, the non-ordered porous material has a pore volume of at least about 0.5 cc/g, or at least about 0.6 cc/g, or at least about 0.7 cc/g, or at least about 0.8 cc/g, or at least about 0.9 cc/g, or at least about 1.0 cc/g, or from at least about 0.5 cc/g up to about 3.0 cc/g. In a further embodiment, the non-ordered porous material has a surface area (i.e., a BET surface area as measured by nitrogen adsorption) of about 350 m²/g to about 1400 m²/g, or greater, or from about 400 m²/g to about 1300 m²/g or greater. In other embodiments, the inorganic oxide material may have a pore size distribution relative span of at least about 0.4, at least about 0.5, at least about 0.6, at least about 0.7, at least about 0.8, at least about 0.9, at least about 1.0, or at least about 1.1. In further embodiments, the inorganic oxide materials may have a pore size distribution relative span of at least about 0.4, at least about 0.5, at least about 0.6, at least about 0.7, at least about 0.8, at least about 0.9, at least about 1.0, or at least about 1.1, up to about 2.0.

In some other embodiments, the non-ordered porous material has (i) a mean pore diameter of from about 50 angstroms to about 100 angstroms, (ii) a pore volume of about 0.7 cc/g to 2.5 cc/g, or greater, and (iii) a surface area of about 400 m²/g to about 1400 m²/g, or greater.

In some other embodiments, the non-ordered porous material used in the present invention has a desired pore volume that varies depending on the surface area, and a desired surface area depending on the pore volume. For example, in some desired embodiments, as the pore volume of the non-ordered porous material increases above about 0.5 cc/g, the surface area ranges from (1) a lower surface area amount represented by a sum of 300 m²/g plus about 27 m²/g per 0.1 cc/g increase in the pore volume above 1.1 cc/g, and (2) an upper surface area amount represented by a sum of 800 m²/g plus about 160 m²/g per 0.1 cc/g increase in the pore volume above 0.5 cc/g.

In other embodiments, the non-ordered porous material used in the present invention also has a specific surface area of about 500 m²/g to about 1400 m²/g, or greater, or from about 600 m²/g to about 1200 m²/g, or greater.

The compositions of the present invention are also directed to pharmaceutical compositions. In one exemplary embodiment, the present invention is directed to a pharmaceutical composition comprising at least one pharmaceutical dosage formulating ingredient; and a drug release composition comprising a biologically active material and an inorganic oxide material, wherein the inorganic oxide material comprises a non-ordered porous material comprising (i) pores having a mean pore diameter of about 25 angstroms to about 150 angstroms; (ii) pores having a pore volume, as measured by nitrogen porosimetry, of about 0.5 cc/g or greater; and (iii) a BET surface area, as measured by nitrogen adsorption, of about 300 m²/g or greater.

When used in pharmaceutical compositions, the inorganic oxide material desirably has (i) a mean pore diameter is about 40 angstroms to about 100 angstroms, more desirably, from about 50 angstroms to about 100 angstroms; (ii) a pore volume of about 0.6 cc/g to about 2.5 cc/g, or greater, more desirably, about 0.7 cc/g to about 2.0 cc/g, or greater, and (iii) a surface area of about 350 m²/g to about 1400 m²/g, or greater, more desirably, about 400 m²/g to about 1200 m²/g, or greater.

Further, when used in pharmaceutical compositions, the inorganic oxide material desirably has a pore volume and surface area that correspond with one another according to the following criteria: as the pore volume increases above about 0.5 cc/g, the surface area ranges from (1) a lower surface area amount represented by a sum of 300 m²/g plus about 27 m/g per 0.1 cc/g increase in the pore volume above 1.1 cc/g, and (2) an upper surface area amount represented by a sum of 800 m²/g plus about 160 m²/g per 0.1 cc/g increase in the pore volume above 0.5 cc/g.

In addition, when used in pharmaceutical compositions, the inorganic oxide material desirably has a specific surface area of about 500 m²/g to about 1400 m²/g or greater, more desirably, a specific surface area of about 600 m²/g to about 1200 m¹/g or greater.

Although the inorganic oxide material may comprise a variety of inorganic oxide materials, typically, the inorganic oxide material used in the present invention comprises silicon oxide.

The biologically active material used in the compositions of the present invention may comprise any known biologically active material. In some embodiments, the biologically active material comprises at least one active pharmaceutical ingredient (API). In some embodiments, the biologically active material comprises two or more active pharmaceutical ingredients (APIs) in combination with one another. In other embodiments, APIs include those of groups I or IV of the Biophannaceutics Clssification System (BCS) (FDA). Exemplary APIs include, but are not limited to, atorvastatin, amiodarone, candesanan-cilex-etil, carvedilo, clopidogrel bisulfate, dipyridamole, eprosanan mesylate, epierenone, ezetimibe, felodipine, funsemide, isradipine, lovastain, metazone, nicardipine, nisoldipine olmesautan medoxomil, propafenone HO, qinapil, ramipril, simvasatin, telmisatan, trandoapil, valsartan and other cardio-vascular active drugs; acyclovir, adefovir, dipivoxil, amphotericin, amprenavir, cefixime, ceftazidime, clarithromycin, clotrimazole, efavirenz, ganciclovir, itraconazole, norfloxacin, nystatin ritonavir, saquinavir and other anti-infective drugs including anti-bacterial, anti-viral, anti-fungal and anti-parasitic drugs; cisplatin, carboplatin, docetaxel, etoposide, exemestane, idarubicin, irinotecan, melphalan, metcaptopurine, mitotane, paclitaxel, valrubicin, vincristine and other drugs used in oncology; azathioprine, tacrolimus, cyclosporine, pimecrolimus, siroimus and other immonosupressive drugs; clozapine, entacapone, fluphenazine, imipramine, nefazodone, olanzapine, paroxetine, pimozide, semraline, triazolam, zaleplon, zipusidoneand, risperidone, carbamazepine and other drugs for CNS indications; danazol, dutasteride, medroxyprogesterone, estradiol, raloxifene, sildenafil, tadalafil, testosterone, vandemafil and other drugs used for reproductive health; celecoxib, dihydroergotamine mesylate, eletriptan, ergoloidmesylales, ergotamine-tartrate, nabumetone, ibupsfen, ketopnofen, triamcinolone, triamcinolone acetonide and other anti-inflammatory and analgesic drugs; bosentan, budesonide, desloratadine, fexofenadin, fluticasone, loratadine, mometasone, salmeterd xinafoate, triamcinolon acetonide, zafirdukast and other drugs for respiratory indications; and dronabinol, famotidine, glyburide, hyoscyamine, isotretinoin, megestol, mesalamine, modafinil, mosapride, nimodipine, perphenazine, propofol, sucralfate, thalidomide, trizanidine hydrochloride and other drugs for various indications including in particular gastiinwrstdal disoders, diabetes and derrmaruogy indications. In further embodiments the APIs include ezetimimbe glucoroniude, tadalafil, fenofibrate, danazol, itraconazol, carbamazepine, griseofulvin, nifedipin or a combination thereof.

The present invention is further directed to methods of making any of the herein disclosed compositions. In one exemplary embodiment, the method of making a composition of the present invention comprises incorporating at least one biologically active material into inorganic oxide material, wherein the inorganic oxide material comprises a non-ordered porous material comprising (i) pores having a mean pore diameter of about 2.5 nm to about 15.0 nm; (ii) pores having a pore volume, as measured by nitrogen porosimetry, of about 0.5 cc/g to about 3.0 cc/g or greater; and (iii) a BET surface area, as measured by nitrogen adsorption, of about 300 $m^2/g$ to about 1400 $m^2/g$ or greater.

In another embodiment, the method of making a composition of the present invention comprises combining a drug release composition comprising the at least one biologically active material incorporated into the inorganic oxide material with at least one pharmaceutical dosage formulating ingredient so as to form a pharmaceutical composition. As discussed above, the inorganic oxide material comprises a non-ordered porous material comprising (i) pores having a mean pore diameter of about 2.5 nm to about 15.0 nm; (ii) pores having a pore volume, as measured by nitrogen porosimetry, of about 0.5 cc/g to about 3.0 cc/g or greater, and (iii) a BET surface area, as measured by nitrogen adsorption, of about 300 $m^2/g$ to about 1400 $m^2/g$ or greater.

The non-ordered porous material may be in various forms, such as precipitates, gels, fumed, colloidal, etc, and combinations thereof, unmodified or modified by subsequent processes, such as autoclaving, super critical fluid extraction, flash drying and the like. In one embodiment, non-ordered porous inorganic oxide material that is suitable for use in the present invention includes precipitated inorganic oxide particles and inorganic oxide gel particles. These inorganic oxides are referred to herein as "parent inorganic oxides," "parent particles" or "parent dispersions". Even though any inorganic oxide composition may be suitable for use in this invention (e.g., $SiO_2$, $Al_2O_3$, $AlPO_4$, MgO, $TiO_2$, $ZrO_2$ etc.), provided that it is non-ordered, one embodiment of the present invention includes amoaphous precipitated silica and silica gel. The inorganic oxides may also include mixed inorganic oxides including $SiO_2.Al_2O_3$, $MgO.SiO_2.Al_2O_3$, and the like. Mixed inorganic oxides are prepared by conventional blending or cogelling procedures. In embodiments comprising gels, the dispersions are derived from porous inorganic oxide gels such as, but not limited to, gels comprising $SiO_2$, $Al_2O_3$, $AlPO_4$, MgO, $TiO_2$, and $ZrO_2$. The gels can be hydrogels, aerogels, or xerogels. A hydrogel is also known as an aquagel which is formed in water and as a result its pores are filled with water. A xerogel is a hydrogel with the water removed. An aerogel is a type of xerogel from which the liquid has been removed in such a way as to minimize any collapse or change in the gel's structure as the water is removed.

In one embodiment of the present invention, the inorganic oxide gels include non-ordered porous silica gel. Such a silica gel may be prepared by mixing an aqueous solution of an alkali metal silicate (e.g., sodium silicate) with a strong acid such as nitric or sulfuric acid, the mixing being done under suitable conditions of agitation to form a clear silica sol which sets into a hydrogel, i.e., macrogel, in less than about one-half hour. The resulting gel is then washed. The concentration of inorganic oxide, i.e., $SiO_2$, formed in the hydrogel is usually in the range of about 10 and about 50, or between about 20 and about 35, or between about 30 and about 35 weight percent, with the pH of that gel being from about 1 to about 9, or 1 to about 4. A wide range of mixing temperatures can be employed, this range being typically from about 20 to about 50° C. The newly formed hydrogels are washed simply by immersion in a continuously moving stream of water which leaches out the undesirable salts, leaving about 99.5 weight percent or more pure inorganic oxide behind. The pH, temperature, and duration of the wash water will influence the physical properties of the silica, such as surface area (SA) and pore volume (PV). Silica gel washed at 65.90° C. at pH's of 8-9 for 15-36 hours will usually have SA's of 250-400 and form aerogels with PV's of 1.4 to 1.7 cc/gm. Silica gel washed at pH's of 3-5 at 50-65° C. for 15-25 hours will have SA's of 700-850 and form aerogels with PV's of 0.6-1.3. In the present invention, the measurements of pore volume are generated by $N_2$ porosity analysis (ASTM D 4222083) and surface area are generated by the BET technique (ASTM D 3663-84 or DIN 66131).

Methods for preparing inorganic oxide gels such as alumina and mixed inorganic oxide gels such as silica/alumina cogels are also well known in the art, such as by conventional blending, co-gelation, co-precipitation, and the like. Methods for preparing such gels are described in U.S. Pat. No. 4,226,743, the contents of which are incorporated herein by reference. In general, alumina gels are prepared by mixing alkali metal aluminates and aluminum sulfate. Cogels are prepared by cogelling two metal oxides so that the gels are composited together. For example, silica alumina cogels can be prepared by gelling an alkali metal silicate with an acid or acid salt, and then adding alkali metal aluminate, aging the mixture and subsequently adding aluminum sulfate. The gel is then washed using conventional techniques. Another embodiment of this invention is derived from dispersions of certain precipitated inorganic oxides. For example, milling certain precipitated silicas results in dispersions having the porosity properties described later below and illustrated in FIG. 1. Reinforced precipitated silica such as that described in U.S. Pat. No. 4,157,920 can also be used to prepare the dispersion of this invention. The contents of that patent are incorporated herein by reference. For example, reinforced precipitated silicas can be prepared by first acidulating an alkali inorganic silicate to create an initial precipitate. The resulting precipitate is then reinforced or "post conditioned" by additional silicate and acid. The precipitate resulting from the second addition of silicate and acid comprises 10 to 70% by weight of the precipitate initially prepared. It is believed that the reinforced structure of this precipitate is more rigid than conventional precipitates as a result of the second precipitation. Once an inorganic oxide is selected for the parent dispersion, a liquid phase of the selected inorganic oxide is prepared. In general, the parent dispersion should be in a state that can be wet milled. The medium for the liquid phase can be aqueous or non-aqueous, e.g., organic. The liquid phase can be residual water in inorganic oxide gels which have been drained, but not yet dried, and to which additional water is added to reslurry the gel.

In another embodiment, dried inorganic oxides, e.g., xerogels, are dispersed in liquid medium. In yet another embodiment, the inorganic oxide can be dispersed in a liquid compound which is subsequently used as a reactant or solvent or medium, which forms the biologically active composition of the present invention. In some embodiments, the parent dispersion is then milled. The milling is conducted "wet", i.e., in liquid media. The general milling conditions can vary depending on the feed material, residence time, impeller speeds, and milling media particle size. The techniques for selecting and modifying these conditions to obtain the desired dispersions are known to those skilled in the an. The milling equipment used to mill the parent inorganic oxide particles should be of the type capable of severely milling and reducing materials to particles having the desired size, e.g., through mechanical action. Such mills are commercially available, with fluid energy mills, hammer mills, and sand mills being particularly suitable for this purpose. Hammer mills impart the necessary mechanical action through high speed metal blades, and sand mills impart the action through rapidly churning media such as zirconia or sand beads. Impact mills can also be used. Both impact mills and hammer mills reduce particle size by impact of the inorganic oxide with metal blades. A dispersion comprising particles of three microns or smaller is then recovered as the final product. In other embodiments, milling is not needed, such as for air-set inorganic oxide gels. Such gels are formed by air-spraying an intimate mixture of an alkali metal solution (e.g., sodium silicate) with a suitable acid (e.g., sulfuric acid) at such a concentration so that mixture gels during flight, before being collected in a suitable medium, generally water. Any resulting dispersion or powder may also be further processed. For example, further processing is desirable if there is a need to prepare a relatively stable dispersion without the aid of dispersing agents, or if there is a significant population of particles that are larger than desired. Further processing may also be needed to insure that essentially all of the distribution of particles is below a certain size. In such a case, the dispersion or powder is processed to separate the smaller particles from the larger particles. This separation can be created by centrifuging the inorganic oxide particles into a supernatant phase, which comprises the smaller particles of the final product, and a settled phase which comprises the larger particles. The supernatant phase is then removed from the settled phase, e.g., by decanting. Conventional centrifuges can be used for this phase separation. In some instances, it may be preferable to centrifuge the supernatant two, three or more times to further remove large particles remaining after the initial centrifuge. It is also contemplated that the larger particles of a milled dispersion can separate over time under normal gravity conditions, and the supernatant can be removed by decanting. Depending on the product particle size targets, the settled phase also can be regarded as the particles of this invention. The dispersion of particles or powder also can be modified after milling to insure a stable dispersion. This can be accomplished through pH adjustment, e.g., adding alkaline material, or by the addition of conventional dispersants.

In the methods of making a composition of the present invention, the step of incorporating at least one biologically active material into inorganic oxide material typically comprises a variety of API loading mechanisms, including a solvent method, an incipient wetness method, a melt method, and any combinations thereof.

In one embodiment of the present invention, the API is incorporated into the inorganic oxide material by means of impregnation with solution of the API in a volatile solvent system. Typically, the inorganic oxide material is dried for 30 minutes at 150° C. to remove physically adsorbed water. Subsequently, the inorganic oxide material is impregnated with a solution of the API in a volatile solvent system. The concentration of the API in the solution is typically between 5-500 mg/ml. Solvent systems may consist of pure solvents ore mixtures of solvents. Solvents may include aliphatic alcohols (e.g. methanol, ethanol, propanol, isopropanol), chlorinated hydrocarbons (e.g. methylene chloride, chloroform, trichlaroethane, carbon tetrachloride), fluorinated alcohols (e.g. hexafluoroisopopanol), acetone, twahydrofuran, ethylacetate, acetonitrile, and combinations thereol After impregnation, the solvent is removed by evaporation, which may achieved under reduced pressure (e.g. 0.001 bar) and elevated temperature (e.g. 40, 50 or 60° C.).

In another embodiment of the present invention, the melt method includes a physical mixture of a biologically active species and a non-ordered porous inorganic oxide based material in the form of a powder or slurry with the desired drug loading weight ratio (e.g., up to about 30% drug by weight), which is prepared and heated at high temperature (e.g. 190° C.) for a relatively short period of time (e.g. 5 minutes). After this initial heating, the mixture may optionally be quickly shaken and heated again at a similarly high temperature for a similar period of time. After cooling, the resulting powders may then be stored, preferably under reduced pressure (e.g. $10^{-3}$ bar) at about 40° C., for a significant period of time (e.g. 48 hours). An example of the "melt method" comprises for instance preparing a physical mixture of itraconazole and a non-ordered porous inorganic oxide material (e.g., non-ordered porous silica powder or slurry) with an itraconazole/non-ordered porous inorganic oxide weight ratio from about 30:70 to about 20:80, and heating at 190° C. for 5 minutes. After this initial heating, the mixture is shaken quickly and placed back at 190° C. for 5 minutes. The powders are stored for 48 hours under reduced pressure ($10^{-3}$ bar) at 40° C.

The methods of making the compositions of the present invention may comprise one or more additional steps including, but not limited to, formulating the compositions containing a biologically active material and a non-ordered inorganic oxide material into a final dosage form. The final dosage form will vary depending upon the manner in which it is administered to the patient. For example, they may be in liquid dosage form, solid dosage form and semisolid dosage forms. Oral dosage forms include those for enteral, buccal, sublabial, sublingual and respiratory tract applications. Enteral or digestive tract dosage forms may include solid dosage forms such as, pill, tablet, capsule, time release technology, drug Buccal, sublabial, or sublingual dosage forms may include solid (e.g., orally disintegrating tablet, film, lollipop, lozenges, chewing gum, etc.) Dermal dosage forms include liquid and solid forms (e.g., ointment, liniment, paste, film, hydrogel, cream, lotion, lip balm, medicated shampoo, dermal patch, transdermal patch, transdermal spray).

In one embodiment of the present invention, the compositions containing a biologically active material and a non-ordered inorganic oxide material into a final oral dosage form, such as a pill or tablet. This may include one or more pharmaceutically acceptable excipients, and may be suitable for providing immediate or fast in vivo release of said biologically active species, or may be suitable for drug release. Furthermore, it may comprise at least one supersetu-ration-stabilizing agent, e.g., HPMCE5, PVPK-30. Regardless of the production method used to prepare the compositions containing a biologically active material and a non-ordered inorganic oxide material, whether it is solvent-based or solventless, when the final dosage form comprises one or more pharmaceutically acceptable excipients, they may be introduced at any time during the process, including the step designed to load the biologically active material into the poses of the non-ordered inorganic oxide material, or afterwards in a separate step. The pharmaceutical compositions used in the present invention may further comprise one or more pharmaceutically acceptable excipients selected, for example, from hydrocolloids (such as xanthan gum), binding agents, glidants, lubricants, surfactants and diluents. The term "pharmaceutically acceptable excipients" as used herein is intended to refer to any material which is inert in the sense that it does not have any therapeutic and/or prophylactic effect per se but does not adversely interfere with the therapeutic or prophylactic property of the drug or biologically active species or pharmaceutical ingredient being formulated. The nature and amount of such excipients are not critical to the present invention. They include for instance diluents such as lactose, calcium carbonate, dextrose or microcrystalline cellulose, binding agents such as starch, gelatin, water-soluble acrylic (co) polymers, polyvi-nyl-pyrrolidone, polyaminoacids, ethylene-vinyl acetate copolymers and the like; disintegrants such as crosslinked sodium carboxymethylcellulose;

The present invention is even further directed to methods of using any of the herein disclosed compositions. In some embodiments, the compositions of the present invention may be used as medicaments. The present invention relates in another particular aspect to the pharmaceutical composition according to the invention for the use as a medicament wherein the composition is applied orally, subcutaneously, intramusculary or intravenously. In some embodiments, the method of using a composition of the present invention comprises administering a composition to a patient so as to deliver at least one biologically active material to the patient, wherein the composition comprises the at least one biologically active material and an inorganic oxide material, wherein the inorganic oxide material comprises a non-ordered porous material comprising pores having a mean pore diameter of about 25 angstroms to about 150 angstroms; pores having a pore volume, as measured by nitrogen porosimetry, of about 0.5 cc/g or greater; and a BET surface area, as measured by nitrogen adsorption, of about 300 m$^2$/g or greater. For example, in some embodiments, the compositions according to the present invention may be administered by various means, including by oral, buccal, sublingual, periodontal, vaginal, rectal, transdermal and topical means.

The methods of using the compositions of the present invention may comprise one or more additional steps including, but not limited to, administering the pharmaceutical composition, which are well known in the art.

It has been found that the non-ordered porous materials used in the present invention provide desirable dissolution rate profiles for a variety of biologically active materials (e.g., APIs) such that the API is released at concentrations that are not achievable by dissolution of the API in crystalline form.

In some embodiments, exposure of a therapeutic dose of the API to a physiologically relevant volume of a physiologically relevant medium (i.e., a medium that is representative of the human gastrointestinal fluids) gives rise to supersaturation concentrations that are in excess of those that can be obtained by dissolution of the crystalline drug form, such that the area under the concentration versus time profile recorded during an in vitro experiment is equal to or higher than that of the crystalline form, or 2 to 10 times higher, or 3 to 10 times higher, or 5 to 10 times higher. Dissolution rates may be measured by in vitro testing using a medium and conditions that simulate in vivo conditions in humans. For example, the testing may be conducted by dispersing an accurately weighed quantity of API-loaded inorganic oxide material in a fixed volume of release medium, such as SGF or FaSSIF, in order to simulate gastrointestinal conditions, followed by collection of multiple samples at predetermined time points. The inorganic oxide material is then removed by filtering, after which the filtrate (i.e., medium) is assayed for API concentration using a validated HPLC method.

It should be understood that the inorganic oxide material may comprise two or more different and distinct types of non-ordered porous material with each distinct type of non-ordered porous material providing a specific dissolution profile for a single biologically active material (or two or more different biologically active materials) so as to form a composite dissolution profile for the single biologically active material (or two or more different biologically active materials). A given composite dissolution rate profile for a single biologically active material (or two or more different biologically active materials) provides a greater overall dissolution rate over time for the single biologically active material (or two or more different biologically active materials) compared to any specific dissolution rate profile for any type of non-ordered porous material.

The present invention is described above and further illustrated below by way of examples, which are not to be construed in any way as imposing limitations upon the scope of the invention. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

In these Examples, the non-ordered inorganic oxide material utilized is silica. However, any inorganic oxide material may be used, provided such materials possess the physical properties described herein. The silica samples (Sample 1, 2 and 3) of the present invention selected for use in the Examples are made using the following process: 190 g of a 19% sulfuric acid solution was placed in a reactor equipped with an overhead stirrer and chilled to 5° C. Separately, 263 g of a solution of sodium silicate (22.9% SiO$_2$) was also chilled to 5° C. Subsequently, the sodium silicate solution was added to the sulfuric acid solution via a pump at such a rate as to add the full quantity of silicate in 15 minutes. During the addition the temperature was maintained at 5° C. After the addition was completed, the reactor was warmed to room temperature and the contents were allowed to gel without stirring. Upon gelation, the gel mass was cut in small pieces and submerged in water, in order to remove the sodium sulfate formed during the reaction. The level of sodium sulfate remaining in the material was periodically checked, as wash water was drained and fresh water was added to the gel. When the level fell below 1% the gel was suspended in water and the pH of the liquid was adjusted to pH=9.7 and the solution heated to 67° C. The temperature was maintained for 20 hours and 20 minutes. At the end of the heating period the gel was recovered by filtration and dried in a 160° C. oven until the moisture content of the gel was less than about 5% by weight. The silica gel thus obtained had a nitrogen BET surface area of 325 m$^2$/g and a nitrogen pore volume of 1.24 cc/g. Assuming cylindrical pores and using the equation: Pore Size (Angstroms) =40000XPV/SA this material exhibits a pore size of 153 Angstroms. Subsequently, the gel is milled to the desired particle size (75 microns) using an ACM and then hydrothermally treated in an autoclave at 300° C. until the desired pore size is achieved.

The following silica particles shown in Table 1 below were used in the examples of the present invention.

TABLE 1

Silica Particle Properties

| Identification | Sample 1 | Sample 2 | Sample 3 |
|---|---|---|---|
| Malvern | | | |
| D10 (μm) | 5.8 | 2.5 | 5.6 |
| D50 (μm) | 10.9 | 7.0 | 12.1 |
| D90 (μm) | 19.1 | 15.2 | 21.2 |
| Pore Size (nm) Desorption (BJH) | 7.02 | 6.74 | 3.76 |
| PV (ml/g) | 0.92 | 1.31 | 0.62 |
| BET SA (m$^2$/g) | 522 | 798 | 737 |
| APD (Calc) (Å) | 70 | 65 | 34 |

The particle sizes reported in the Examples were determined by light scattering using a Malvern Mastersizer 2000 available from Malvern Instruments Ltd. per ASTM B822-10. Pore size distributions are measured by mercury intrusion using an Autopore IV 9520 available from Micromeritics Instrument Corp. Pore volumes referenced herein represent mercury intrusion into pores 10,000 A and below. Pore size distributions are also measured by nitrogen sorption (BJH method) using a Tristar 3000 also available from Micromeritics Instrument Corp. BET surface areas are also obtained from the nitrogen sorption analysis.

In all the below examples, the APIs were loaded onto the silica materials via solvent impregnation. Prior to loading, all silica materials were dried at 150° C. for at least 1 hour to remove physically adsorbed water. Subsequently, the silica materials were allowed to cool down to room temperature, after which they were manually impregnated with a concentrated (20-150 mg/ml) API solution in methylene chloride. After impregnation, samples were dried under reduced pressure (10$^{-3}$ bar) for at least 4 hours to remove the solvent.

The total API content in the loaded silica powders was determined by extraction of the API from the silica materials using methanol. An accurately weighed quantity of API-loaded silica was weighed into a 20 ml volumetric flask and made up to volume with methanol. After 1 hour of equilibration, the silica was removed by filtration and the filtrate assayed for API using high performance liquid chromatography with ultraviolet detection (HPLC-UV).

In the examples below, all loaded silica powders were devoid of crystalline API as verified using differential scanning calorimetry (DSC).

In all examples, in vitro dissolution testing was conducted by dispersing an accurately weighed quantity of API-loaded silica in a fixed volume of release medium, followed by collection of multiple samples at predetermined time points. All samples were filtered over a 0.45 μm filter to separate silica particles or precipitated drug, after which the filtrate was assayed for API concentration using HPLC. Specific conditions (in terms of dose, volume of medium, composition of medium) are specified for each individual example.

Example 1—Release of a Poorly Water-Soluble Model Compound (Danazol) in Fasted State Simulated Intestinal Fluid (FaSSIF) Under Supersaturating Conditions In this example, danazol-loaded silica powders set forth in Table 2 below were dispersed in FaSSIF, under supersaturating conditions (i.e. under conditions whereby complete release of the danazol load is associated with the generation of concentrations that are in excess of the equilibrium solubility). A quantity of loaded silica powder equivalent to a 2 mg danazol dose was dispersed in 40 ml of FaSSIF.

TABLE 2

Danazol content of loaded silica materials used in Example 1.

| Silica | Total danazol content in loaded silica powder (w/w %) |
|---|---|
| 1 | 9.1 |
| 2 | 12.3 |
| 3 | 12.1 |

FIG. 1 graphically displays in vitro release profiles over time of danazol from the exemplary silica/danazol combinations shown in Table 2 above. As shown in FIG. 1, Example 1 illustrates that all three silica materials tested were capable of releasing danazol at concentrations that are well in excess of its equilibrium solubility in FaSSIF (indicated by the dotted line in FIG. 1).

Example 2—Release of a Poorly Water-Soluble Model Compound (Itraconazole) in Simulated Gastric Fluid (SGF) Under Supersaturating Conditions In this example, itraconazole-loaded silica powders set forth in Table 3 below were dispersed in SGF, under supersaturating conditions (i.e. under conditions whereby complete release of the itraconazole load is associated with the generation of concentrations that are in excess of the equilibrium solubility). A quantity of loaded silica powder equivalent to a 2 mg itraconazole dose was dispersed in 20 ml of SGF.

TABLE 3

Itraconazole content of loaded silica materials used in Example 2.

| Silica | Total itraconazole content in loaded silica powder (w/w %) |
|---|---|
| 1 | 20.1 |
| 2 | 19.7 |
| 3 | 16.8 |

Figure 2:
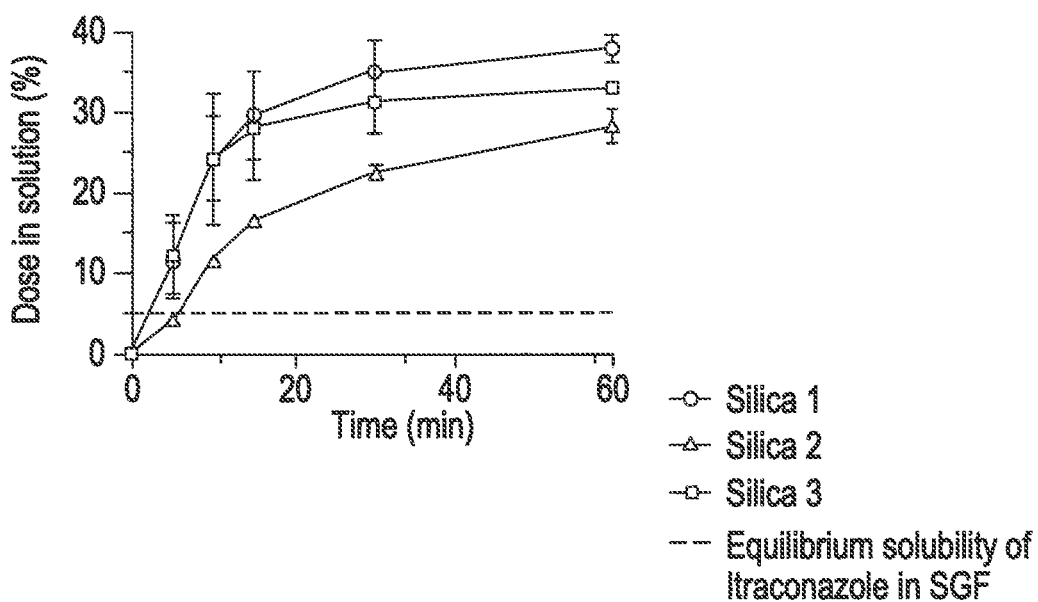
FIG. 2 graphically displays the rate of dissolution over time of another exemplary API, itraconazole, from various exemplary non-ordered silicas of the present invention.

FIG. 2 graphically displays in vitro release profiles over time of itraconazole from the exemplary silica/itraconazole combinations shown in Table 3 above. As shown in FIG. 2, Example 2 illustrates that all three silica materials tested were capable of releasing itraconazole at concentrations that are well in excess of its equilibrium solubility in SGF (indicated by the dotted line in FIG. 2).

Example 3—Release of a Poorly Water-Soluble Model Compound (Fenofibrate) in Fasted State Simulated Intestinal Fluid (FaSSIF) Under Sink Conditions In this example, fenofibrate-loaded silica powders set forth in Table 4 below were dispersed in FaSSIF, under sink conditions (i.e. under conditions whereby complete release of the fenofibrate load is associated with the generation of concentrations that are below the equilibrium solubility). A quantity of loaded silica powder equivalent to a 0.8 mg fenofibrate dose was dispersed in 20 ml of FaSSIF.

TABLE 4

Fenofibrate content of loaded silica materials used in Example 3.

| Silica | Total fenofibrate content in loaded silica powder (w/w %) |
|---|---|
| 1 | 21.5 |
| 2 | 16.1 |
| 3 | 19.7 |

Figure 3:
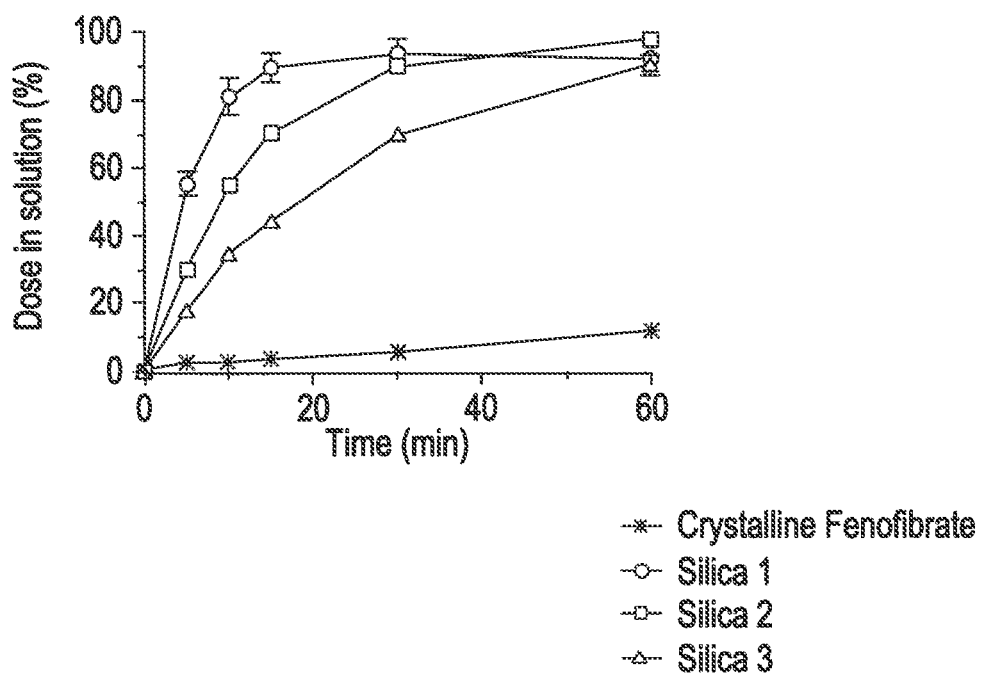
FIG. 3 graphically displays the rate of dissolution over time of another API, fenofibrate, from various exemplary non-ordered silicas of the present invention.

FIG. 3 graphically displays in vitro release profiles over time of fenofibrate from the exemplary silica/fenofibrate combinations shown in Table 4 above. As shown in FIG. 3, Example 3 illustrates that all three silica materials tested were capable of releasing fenofibrate at concentrations that are well in excess of dissolution of the crystalline form of the fenofibrate in FaSSIF (indicated by the lower line in FIG. 3).

Example 4: Blending Two Silicas to Obtain a Combined Release Profile

In this example, a mixture of danazol-loaded silica powders set forth in Table 5 below were dispersed in a medium comprising a phosphate buffer solution supplemented with 0.5% Tween 80 (pH 6.5). A quantity of loaded silica powder equivalent to a 1 mg danazol dose was dispersed in 32 ml of medium.

Figure 4:
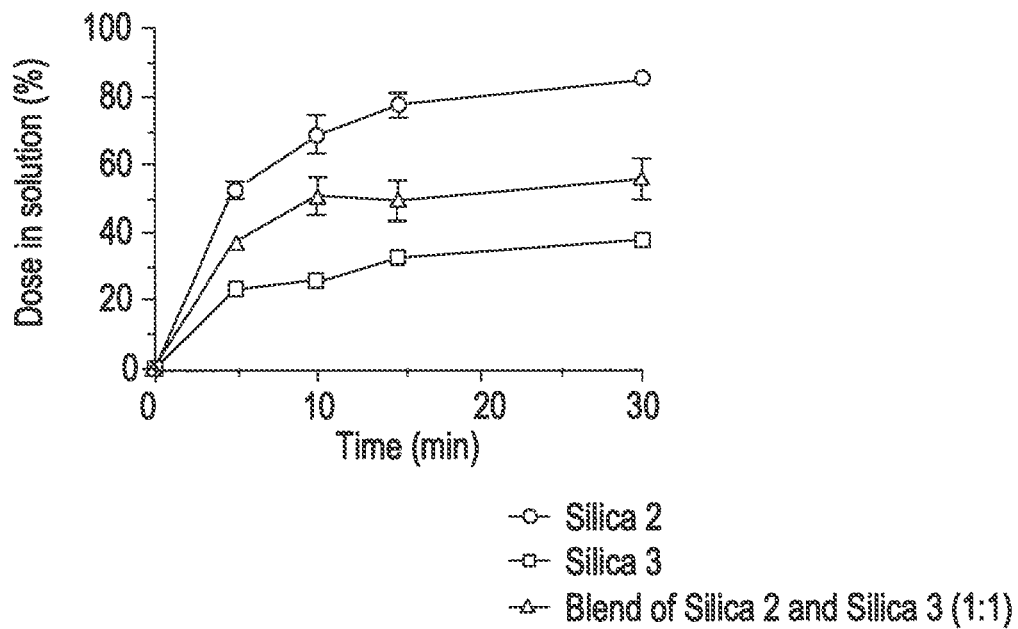
FIG. 4 graphically displays the rate of dissolution over time of danazol from a mixture of two different exemplary non-ordered silicas of the present invention.

Danazol was first loaded on the individual silica materials (Silica 2 and Silica 3), after which both loaded silica powders were blended in a 1:1 ratio. The release profile of the resulting blend is a reflection of the release profiles of its individual constituents (FIG. 4). Such combinations of silica materials enable one to fine tune the release profile according to the requirements of the application.

TABLE 5

Danazol content of loaded silica materials used in Example 4.

| Silica | Total danazol content in loaded silica powder (w/w %) |
|---|---|
| 2 | 22.4 |
| 3 | 22.3 |

FIG. 4 graphically displays in vitro release profiles over time of danazol from the exemplary mixture of two different silica/danazol combinations shown in Table 5 above. As shown in FIG. 4, Example 4 illustrates how two silicas can be used as a combination, thereby giving rise to a new concentration-time profile.

While the invention has been described with a limited number of embodiments, these specific embodiments are not intended to limit the scope of the invention as otherwise described and claimed herein. It may be evident to those of ordinary skill in the art upon review of the exemplary embodiments herein that further modifications, equivalents, and variations are possible. All parts and percentages in the examples, as well as in the remainder of the specification, are by weight unless otherwise specified. Further, any range of numbers recited in the specification or claims, such as that representing a particular set of properties, units of measure, conditions, physical states or percentages, is intended to literally incorporate expressly herein by reference or otherwise, any number falling within such range, including any subset of numbers within any range so recited. For example, whenever a numerical range with a lower limit, $R_L$, and an upper limit $R_U$, is disclosed, any number R falling within the range is specifically disclosed. In particular, the following numbers R within the range are specifically disclosed: $R=R_L+k(R_U-R_L)$, where k is a variable ranging from 1% to 100% with a 1% increment, e.g., k is 1%, 2%, 3%, 4%, 5% ... 50%, 51%, 52% ... 95%, 96%, 97%, 98%, 99%, or 100%. Moreover, any numerical range represented by any two values of R, as calculated above is also specifically disclosed. Any modifications of the invention, in addition to those shown and described herein, will become apparent to those skilled in the art from the foregoing description and accompanying drawings. Such modifications are intended to fall within the scope of the appended claims. All publications cited herein are incorporated by reference in their entirety.

What is claimed is:

1. A composition comprising a biologically active material and an inorganic oxide material, wherein the inorganic oxide material comprises a non-ordered porous material comprising:
   pores having a mean pore diameter of about 2.5 nm to about 10 nm, as calculated assuming the pores are cylindrical;
   pores having a pore volume, as measured by nitrogen porosimetry, of about 0.5 cc/g or greater; and
   a BET surface area, as measured by nitrogen adsorption, of about 300 m$^2$/g or greater.

2. The composition according to claim 1, wherein the pore volume is about 0.6 cc/g or greater.

3. The composition according to claim 1, wherein the surface area is about 350 m$^2$/g or greater.

4. The composition according to claim 1, wherein (i) the mean pore diameter is about 5.0 nm to about 10.0 nm, (ii) the pore volume is about 0.7 cc/g or greater, and (iii) the surface area is about 400 m$^2$/g or greater.

5. The composition according to claim 1, wherein as the pore volume increases above about 0.5 cc/g, the surface area ranges from (1) a lower surface area amount represented by a sum of 300 m²/g plus about 27 m²/g per 0.1 cc/g increase in the pore volume above 1.1 cc/g, and (2) an upper surface area amount represented by a sum of 800 m²/g plus about 160 m²/g per 0.1 cc/g increase in the pore volume above 0.5 cc/g, or as the pore volume increases above about 0.7 cc/g, the surface area ranges from (1) a lower surface area amount represented by a sum of 400 m²/g plus about 40 m²/g per 0.1 cc/g increase in the pore volume above 1.0 cc/g, and (2) an upper surface area amount represented by a sum of 560 m²/g plus about 84 m²/g per 0.1 cc/g increase in the pore volume above 0.7 cc/g.

6. The composition according to claim 1, wherein the non-ordered porous material further comprises a specific surface area is about 500 m²/g or greater.

7. The composition according to claim 1, wherein the in vitro dissolution rate of the biologically active material is at least about 2 times higher than the dissolution rate of the biologically active material in crystalline form.

8. The composition according to claim 1, wherein said non-ordered porous material have a pore size distribution relative span of at least about 0.4.

9. The composition according to claim 1, wherein the inorganic oxide material comprises two or more different and distinct types of non-ordered porous material.

10. The composition according to claim 1, wherein the inorganic oxide material further comprises at least one ordered porous material.

11. The composition according to claim 1 further comprising at least one pharmaceutical dosage formulating ingredient.

12. The composition according to claim 1, wherein the biologically active material comprises at least one active pharmaceutical ingredient (API).

13. The composition according to claim 1, wherein the biologically active material comprises ezetimimbe, tadalafil, or fenofibrate.

14. The composition according to claim 1, wherein the inorganic oxide material comprises silicon oxide.

15. A composition comprising a biologically active material and an inorganic oxide material, wherein the inorganic oxide material comprises two or more different and distinct types of porous material, a first porous material comprising at least one type of non-ordered porous material and a second porous material comprising at least one type of ordered porous material, the non-ordered porous material comprising:
    pores having a mean pore diameter of about 2.5 nm to about 10 nm, as calculated assuming the pores are cylindrical;
    pores having a pore volume, as measured by nitrogen porosimetry, of about 0.5 cc/g or greater; and
    a BET surface area, as measured by nitrogen adsorption, of about 300 m²/g or greater.

16. The composition according to claim 15, wherein each of the first and second porous materials provide a specific dissolution rate profile for the biologically active material so as to form a composite dissolution rate profile for the biologically active material.

17. The composition according to claim 15, wherein the in vitro dissolution rate of the biologically active material is at least about 2 times higher than the dissolution rate of the biologically active material in crystalline form or its equilibrium solubility, or the in vitro dissolution rate of the biologically active material is at least about 2 to about 10 times higher than the dissolution rate of the biologically active material in crystalline form.

18. The composition according to claim 15, wherein said non-ordered porous material have a pore size distribution relative span of at least about 0.4.

19. The composition according to claim 1, wherein the biologically active material comprises one selected from groups II or IV of the Biopharmaceutics Classification System.

20. The composition according to claim 15, wherein the biologically active material comprises one selected from groups II or IV of the Biopharmaceutics Classification System.

21. A composition comprising a biologically active material and an inorganic oxide material, wherein the inorganic oxide material comprises a non-ordered porous material comprising:
    pores having a mean pore diameter of about 2.5 nm to about 10 nm, as calculated assuming the pores are cylindrical;
    pores having a pore volume, as measured by nitrogen porosimetry, of about 0.5 cc/g or greater; and
    a BET surface area, as measured by nitrogen adsorption, of about 300 m²/g or greater,
    wherein the biologically active material comprises one selected from groups II or IV of the Biopharmaceutics Classification System.

22. A composition comprising a biologically active material and an inorganic oxide material, wherein the inorganic oxide material comprises two or more different and distinct types of porous material, a first porous material comprising at least one type of non-ordered porous material and a second porous material comprising at least one type of ordered porous material, the non-ordered porous material comprising:
    pores having a mean pore diameter of about 2.5 nm to about 10 nm, as calculated assuming the pores are cylindrical;
    pores having a pore volume, as measured by nitrogen porosimetry, of about 0.5 cc/g or greater; and
    a BET surface area, as measured by nitrogen adsorption, of about 300 m²/g or greater,
    wherein the biologically active material comprises one selected from groups II or IV of the Biopharmaceutics Classification System.

* * * * *